United States Patent
Mak et al.

(10) Patent No.: US 11,701,004 B2
(45) Date of Patent: *Jul. 18, 2023

(54) MULTI-FIBER OPTICAL PROBE AND OPTICAL COHERENCE TOMOGRAPHY SYSTEM

(71) Applicant: SYNAPTIVE MEDICAL INC., Toronto (CA)

(72) Inventors: Siu Wai Jacky Mak, Toronto (CA); Arun Victor Jagga, Toronto (CA)

(73) Assignee: Synaptive Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/454,517

(22) Filed: Nov. 11, 2021

(65) Prior Publication Data

US 2022/0071492 A1 Mar. 10, 2022

Related U.S. Application Data

(63) Continuation of application No. 16/167,146, filed as application No. PCT/CA2016/050469 on Apr. 22, 2016, now Pat. No. 11,202,572.

(51) Int. Cl.
*G01B 9/02091* (2022.01)
*A61B 5/00* (2006.01)
(Continued)

(52) U.S. Cl.
CPC ............ *A61B 5/0066* (2013.01); *A61B 90/37* (2016.02); *G01B 9/0205* (2013.01);
(Continued)

(58) Field of Classification Search
CPC .................. A61B 5/0066; A61B 90/37; A61B 2090/3735; G01B 9/02017;
(Continued)

(56) References Cited

U.S. PATENT DOCUMENTS

| | | |
|---|---|---|
| 6,370,422 B1 | 4/2002 | Richards-Kortum |
| 7,417,740 B2 | 8/2008 | Alphonse |

(Continued)

FOREIGN PATENT DOCUMENTS

| | | |
|---|---|---|
| GB | 2567326 | 4/2019 |
| WO | 2017181259 | 10/2017 |

OTHER PUBLICATIONS

PCT International Search Report for PCT/CA2016/050469 dated Dec. 21, 2016.
(Continued)

*Primary Examiner* — Jonathan M Hansen

(57) ABSTRACT

Multichannel optical coherence systems and methods involving optical coherence tomography (OCT) subsystems are operably and respectively connected to optical fibers of a multichannel optical probe, such that each optical fiber forms at least a distal portion of a sample beam path of a respective OCT subsystem. The optical fibers are in optical communication with distal optical elements such that external beam paths associated therewith are directed towards a common spatial region external to the housing. Image processing computer hardware is employed to process OCT signals obtained from the plurality of OCT subsystems to generate an OCT image dataset comprising a plurality of OCT A-scans and process the OCT image dataset to generate volumetric image data based on known positions and orientations of the external beam paths associated with the OCT subsystems.

8 Claims, 20 Drawing Sheets

(51) Int. Cl.
 *A61B 90/00* (2016.01)
 *G01B 9/02* (2022.01)
 *G01B 9/02017* (2022.01)
 *G01B 9/02015* (2022.01)

(52) U.S. Cl.
 CPC ..... *G01B 9/02017* (2013.01); *G01B 9/02027* (2013.01); *G01B 9/02028* (2013.01); *G01B 9/02049* (2013.01); *G01B 9/02085* (2013.01); *G01B 9/02087* (2013.01); *G01B 9/02089* (2013.01); *G01B 9/02091* (2013.01); *A61B 2090/3735* (2016.02)

(58) Field of Classification Search
 CPC ............ G01B 9/02027; G01B 9/02028; G01B 9/02049; G01B 9/0205; G01B 9/02085; G01B 9/02087; G01B 9/02089; G01B 9/02091
 See application file for complete search history.

(56) References Cited

U.S. PATENT DOCUMENTS

| | | | |
|---|---|---|---|
| 7,783,337 | B2 | 8/2010 | Feldman |
| 8,711,364 | B2 | 4/2014 | Brennan |
| 11,202,572 | B2 * | 12/2021 | Mak .................. G01B 9/02017 |
| 2006/0103850 | A1 | 5/2006 | Alphonse et al. |
| 2010/0041986 | A1 | 2/2010 | Nguyen et al. |
| 2012/0229812 | A1 | 9/2012 | Liu |
| 2019/0133448 | A1 | 5/2019 | Mak et al. |
| 2019/0137254 | A1 * | 5/2019 | Trenholm ............ G06N 3/0454 |
| 2019/0182441 | A1 | 6/2019 | Saleh |

OTHER PUBLICATIONS

PCT Written Opinion of the International Searching Authority for PCT/CA2016/050469 dated Dec. 21, 2016.

* cited by examiner

MULTI-FIBER OPTICAL PROBE AND OPTICAL COHERENCE TOMOGRAPHY SYSTEM

CROSS-REFERENCE TO RELATED APPLICATION(S)

This document is a continuation application, claiming the benefit of, and priority to, U.S. patent application Ser. No. 16/167,146, filed on Oct. 22, 2018, and entitled "MULTI-FIBER OPTICAL PROBE AND OPTICAL COHERENCE TOMOGRAPHY SYSTEM, and International Patent Application No. PCT/CA2016/050469, filed on Apr. 22, 2016, and entitled "MULTI-FIBER OPTICAL PROBE AND OPTICAL COHERENCE TOMOGRAPHY SYSTEM, all of which are hereby incorporated by reference herein in their entirety.

FIELD

The present disclosure generally relates to optical coherence tomography, methods for minimally invasive procedures, and image guided medical procedures.

BACKGROUND

Optical coherence tomography (OCT) enables imaging of tissue with depth limited to typically 1-2 mm due to the light absorption and scattering property of tissue.

When building an OCT probe, the probe should be made as small as possible to minimize openings required in the surgical field for probe insertion so that the risk of any possible damage to the patient is reduced. A smaller probe also allows for ease of use inside surgical cavities. Presently, OCT scan heads use a large objective lens and galvanometers, which are large and limit its use to outside the surgical field. This prevents OCT to be used for surgeries that utilize minimal invasive techniques and surgeries that are typically access through endoscopes.

SUMMARY

Multichannel optical coherence systems are disclosed in which optical coherence tomography subsystems are operably and respectively connected to optical fibers of a multichannel optical probe, such that each optical fiber forms at least a distal portion of a sample beam path of a respective optical coherence tomography subsystem. The optical fibers are in optical communication with distal optical elements such that external beam paths associated therewith are directed towards a common spatial region external to the housing. In some example embodiments, image processing computer hardware is employed to process optical coherence tomography signals obtained from the plurality of optical coherence tomography subsystems to generate an optical coherence tomography image dataset comprising a plurality of optical coherence tomography A-scans and process the optical coherence tomography image dataset to generate volumetric image data based on known positions and orientations of the external beam paths associated with the optical coherence tomography subsystems.

Accordingly, in a first aspect, there is provided a multichannel optical coherence system comprising: a plurality of optical coherence tomography subsystems, each optical coherence tomography subsystem comprising a respective optical source and optical detector; and a multichannel optical probe comprising: a housing; and a plurality of single mode optical fibers supported by said housing, wherein a proximal end of each single mode optical fiber is in optical communication with a respective optical coherence system, such that each single mode optical fiber forms at least a distal portion of a sample beam path of a respective optical coherence system; and a plurality of distal optical elements, wherein each distal optical element is in optical communication with a distal end of a respective optical fiber for focusing or collimating optical radiation emitted therefrom along a respective external beam path and for collecting scattered optical radiation that is scattered along the respective external beam path; wherein said plurality of single mode optical fibers and said plurality of distal optical elements are configured such that the external beam paths associated therewith are directed towards a common spatial region residing external to said housing.

In another aspect, there is provided a multichannel optical coherence system comprising: a plurality of optical coherence tomography subsystems, each optical coherence tomography subsystem comprising a respective optical source and optical detector; and a multichannel optical probe comprising: a housing; and a plurality of single mode optical fibers supported by said housing, wherein a proximal end of each single mode optical fiber is in optical communication with a respective optical coherence system, such that each single mode optical fiber forms at least a distal portion of a sample beam path of a respective optical coherence system; and a plurality of distal optical elements, wherein each distal optical element is in optical communication with a distal end of a respective optical fiber for focusing or collimating optical radiation emitted therefrom along a respective external beam path and for collecting scattered optical radiation that is scattered along the respective external beam path; and image processing computer hardware configured to: process optical coherence tomography signals obtained from the plurality of optical coherence tomography subsystems, thereby obtaining an optical coherence tomography image dataset comprising a plurality of optical coherence tomography A-scans; process the optical coherence tomography image dataset to generate volumetric image data based on known positions and orientations of the external beam paths associated with the optical coherence tomography subsystems, wherein said volumetric image data is represented in a common reference frame for rendering a composite volumetric image; and render, on a display, the composite volumetric image.

In another aspect, there is provided a multi-fiber optical probe comprising: a housing; a plurality of single mode optical fibers supported by said housing; and a plurality of distal optical elements, wherein each distal optical element is in optical communication with a distal end of a respective optical fiber for focusing or collimating optical radiation emitted therefrom along a respective external beam path and for collecting scattered optical radiation that is scattered along the respective external beam path; wherein said plurality of single mode optical fibers and said plurality of distal optical elements are configured such that the external beam paths associated therewith are directed towards a common spatial region residing external to said housing.

A further understanding of the functional and advantageous aspects of the disclosure can be realized by reference to the following detailed description and drawings.

DETAILED DESCRIPTION

Figure 1:
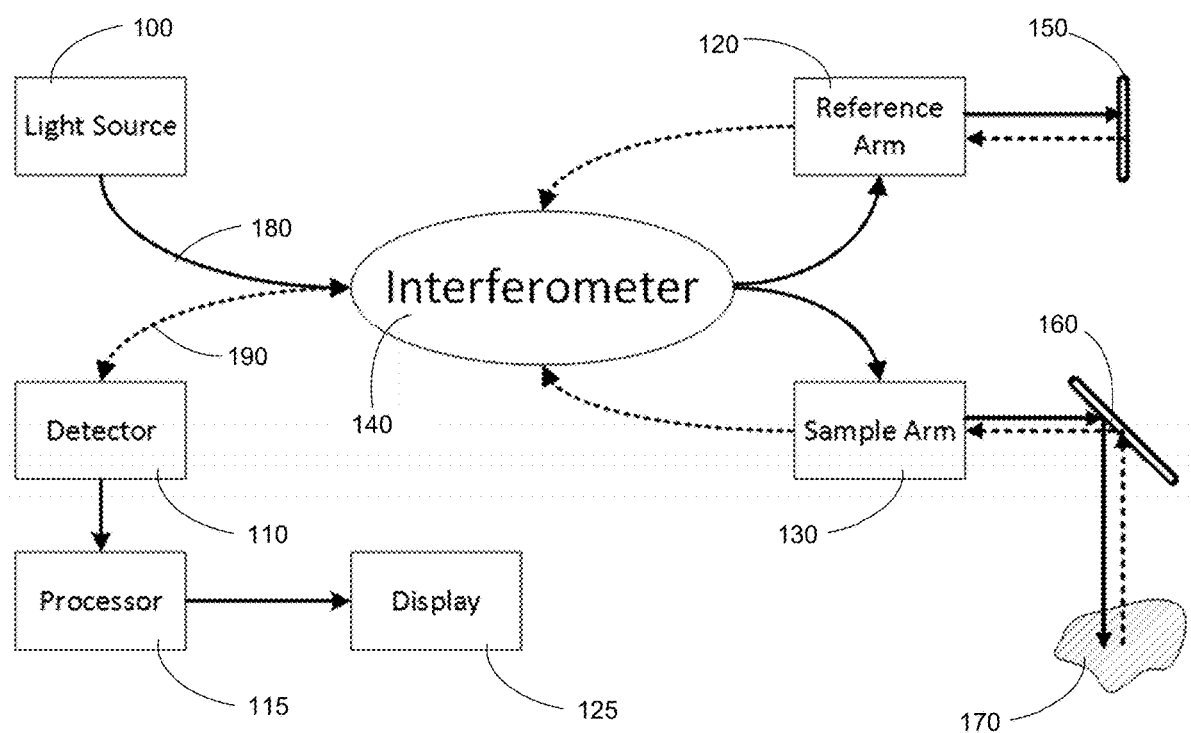
FIG. 1 is a diagram illustrating components of an example OCT system.

Various embodiments and aspects of the present disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

Unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. The surgical process is applicable to surgical procedures for brain, spine, knee and any other suitable region of the body.

Various example embodiments of the present disclosure provide fiber optic probe heads having multiple optical fibers. As shown below, the inclusion of multiple optical fibers in a probe head may be employed to achieve a compact probe head with an effective volumetric scan region while eliminating the need for large motors and/or MEMS scanners. In some example embodiments described below, the multiple fibers may be provided within a probe head and interfaced with one or more optical coherence tomography systems, where the multiple fibers are spatially arranged to probe a plurality of longitudinal spatial segments that can be integrated to provide volumetric information.

Referring to FIG. 1, this diagram illustrates an example OCT system, in accordance with an embodiment of the present disclosure. The system comprises the following elements: a light source 100, a reference arm 120, a sample arm 130, an optical detector 110, and an interferometer 140. The illumination employed by this OCT system generally follows one of two paths. The first path 180, indicated by the solid arrows, is the path along which the interrogating illumination travels; and the second path 190, indicated by the dashed arrows, is the path along which the return illumination travels.

Still referring to FIG. 1, the example OCT system functions in the following way. The light source 100 coupled to the interferometer 140 outputs broadband or narrow band illumination which propagates through the interferometer 140 and is correspondingly split between the sample arm 120 and the reference arm 130 at a given intensity ratio. This ratio is dependent on the choice of interferometer used and may be selected, e.g., optimized, for a given wavelength and configuration of the system. The interrogating illumination, propagating through the reference arm 120, exits via a reference arm optical terminal (not shown) towards a reference mirror 150, subsequently reflects to the optical terminal (not shown) of the reference arm 120, and propagates into the interferometer. The interrogating illumination, propagating through the sample arm 130, exits via an optical terminal (not shown) towards the sample of interest 170 via a directing mechanism 160 (optional). Any interrogation illumination, which is reflected or scattered in the direction of the sample arm 130 after interrogating the sample 170 (termed return illumination henceforth), is then subsequently collected via the sample arm optical terminal (not shown) and the directing mechanism 160 (optional). This return illumination then propagates back through the sample arm into the interferometer 140. The return and reflected illumination from both the sample 130 and the reference 120 arms are then combined at the interferometer 140 where they interfere and produce an optical interference signal.

Still referring to FIG. 1, the optical interference signal then propagates into the detector 110 where it may be subsequently detected, converted from an analog signal to a digital signal, and input to a processor (not shown). The processor may be programmed with instructions to process the input data into a useable format, such as a visualization or graphical representation to be provided to a user. Methods which may be employed to process the OCT data comprise an example of which as provided in the paper [Proc. SPIE 8369, Sensing for Agriculture and Food Quality and Safety IV, 83690F (5 May 2012); doi: 10.1117/12.919347].

Figure 2:
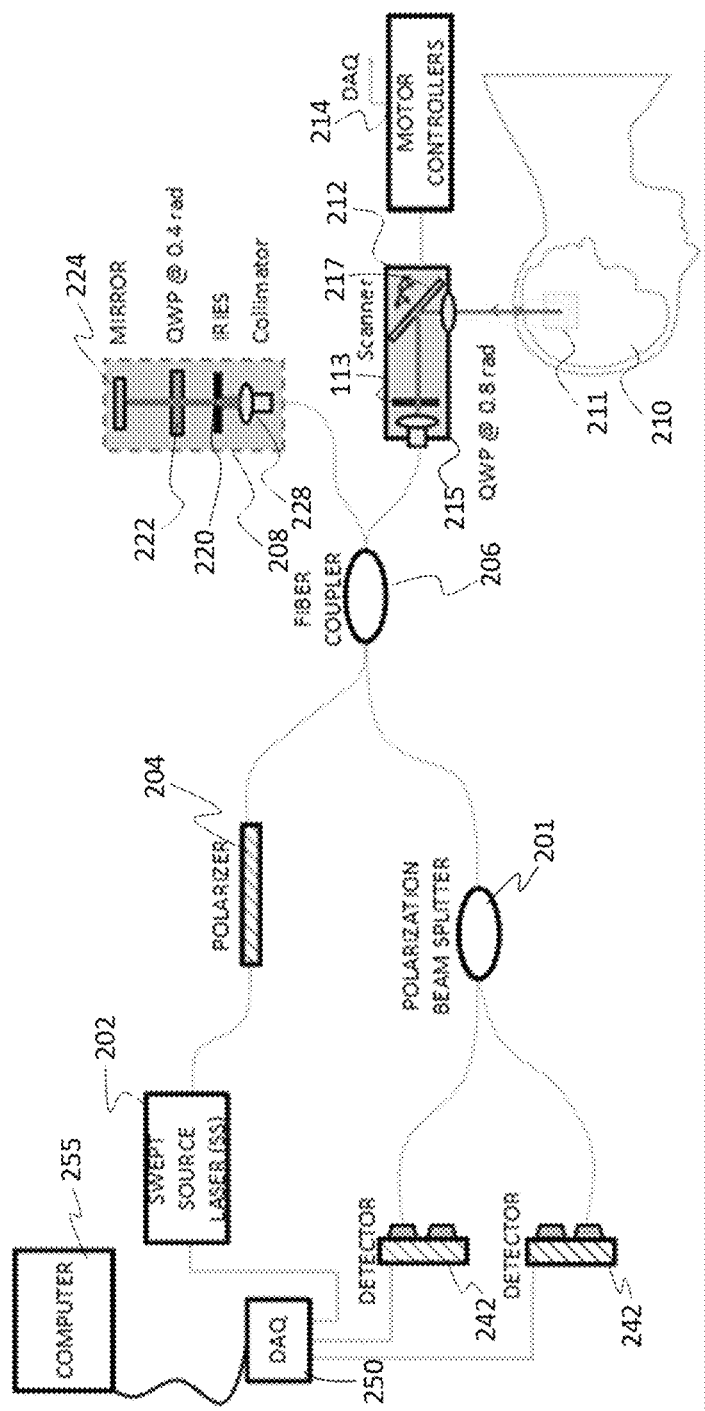
FIG. 2 is a diagram illustrating components of an example PSOCT system.

Referring to FIG. 2, this diagram illustrates a fiber based polarization-sensitive OCT (PS-OCT) system using a frequency sweeping laser source 202, e.g., swept source laser, in accordance with an embodiment of the present disclosure. The light beam from the swept source passes through a polarizer 204 to create a linearly polarized light which subsequently passes through a fiber coupler 206 that splits the power of the input light equally into two arms: a reference arm 208 and a sample arm 212. The light in the sample arm passes through a scanner incorporating a collimator 113 to collimate the light output from the fiber and a quarter-wave plate 215 at 45 degrees which sets the light to a circular polarization state going into the tissue sample. This circularly polarized light can scan across a region 211 in the sample or subject 210 to generate an image through a set of scanning mirrors or galvanometers 217 that are computer-controlled through motor controllers 214. Light reflected and scattered from the tissue sample travels through the quarter-wave plate and is coupled into two orthogonally polarized channels towards the fiber coupler 206.

Still referring to FIG. 2, similar to the sample arm, the light entering the reference arm reflects to the fiber coupler after passing through a similar arrangement of optical components, the main difference being that, in the case of the reference arm, the final element, from which the reflected signal is generated, is a mirror element 224 as opposed to the sample 210 such as that in the sample arm. The components in the reference arm, similar to the sample arm, comprise a collimator 228, a quarter-wave plate 222 at 22.5 degrees, and an iris 220. The quarter-wave plate splits the reference arm power equally between the two orthogonally polarized channels while the iris maximizes the signal-to-noise and resolution of the interferometric signal.

Still referring to FIG. 2, after both signals from the reference and sample arm are generated, the fiber coupler 206 interferes the reflected reference light beam signal and the reflected sample light beam signal and propagates such interfered light signals to a polarizing beam splitter 201 that separates the now interfered light signals into two orthogonal polarization states. Each of the split polarized signals are channeled their respective detectors 242 for conversion from interferometric optical signals into electrical signals. The electrical signals are then subsequently converted into digital signals through a Data Acquisition card (DAQ) 250 which are then stored and processed in the connected computer 255 to generate PSOCT images. The quarter-wave plates in the reference and the sample arm may be interchanged with a polarization controller or a polarization modulator to modulate the light polarization into other states for tissue imaging.

Figure 3:
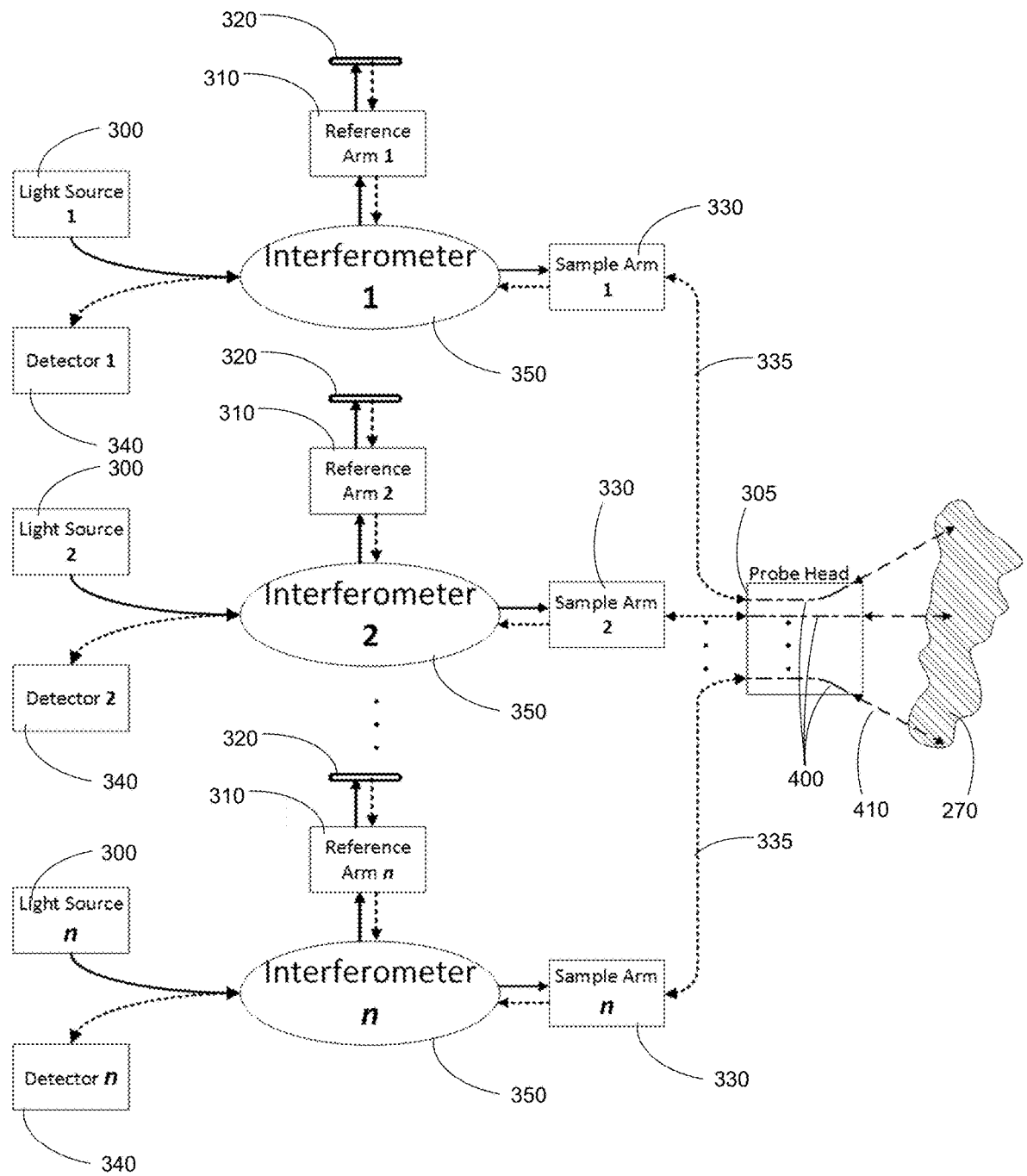
FIG. 3 is a diagram illustrating components of an example OCT system using a probe.
Figure 5A:
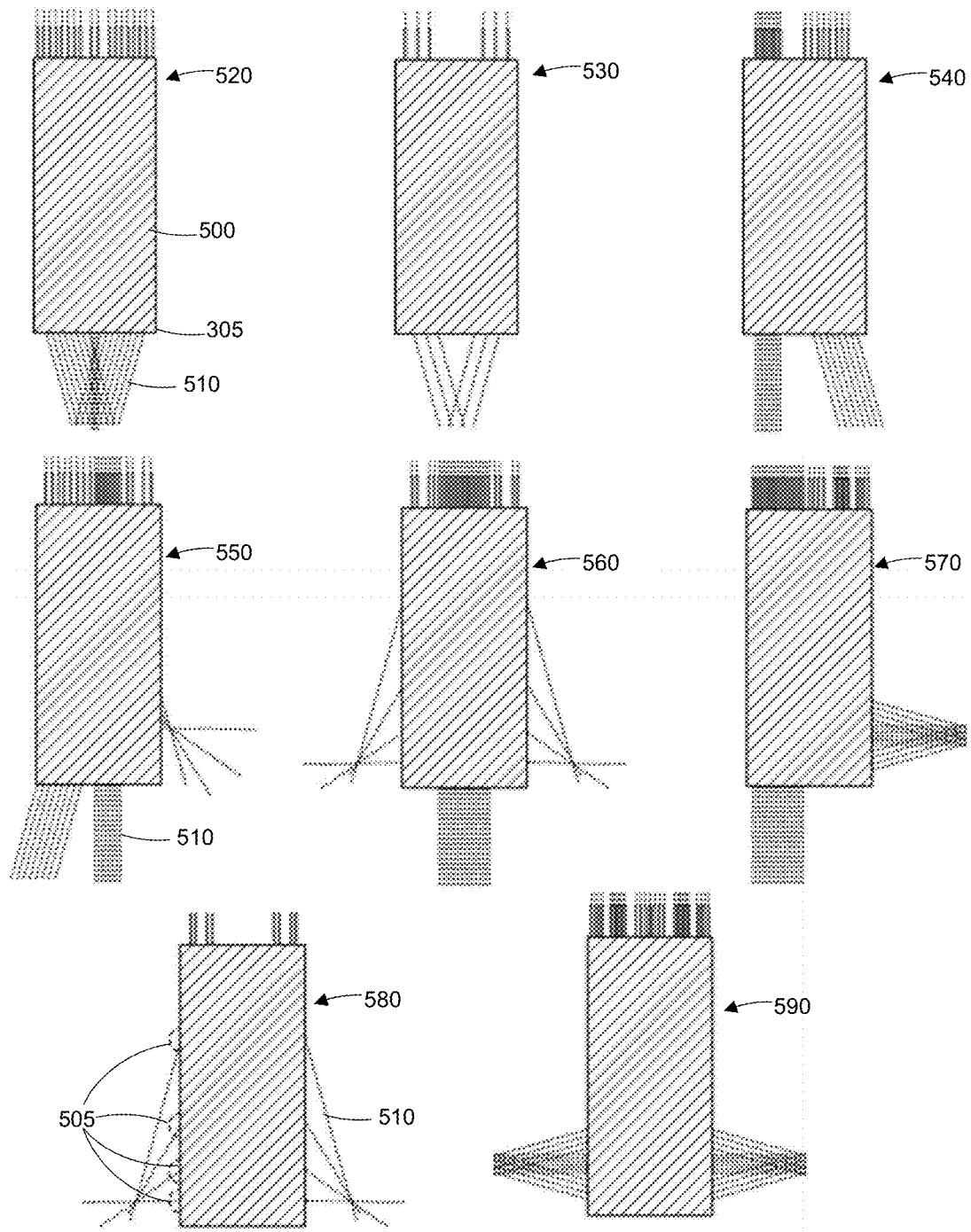
FIG. 5A is a diagram illustrating cross section of various example OCT probe heads.

Referring to FIG. 3, this diagram illustrates a system diagram of an OCT probe system, in accordance with an embodiment of the present disclosure. In the embodiment, the OCT probe comprises n constituent OCT subsystems oriented in a generally parallel arrangement with each of the n constituent OCT subsystems sample arms 400 (for directing and receiving beams 410 to and from tissue 270) being partially or entirely encompassed in a common probe head 305 (example embodiments of which are depicted in FIG. 5A and will be described in further detail below), wherein n=an integer. Each of the individual n constituent OCT subsystems has an individual light source 300, an individual detector 340, an individual interferometer 350, an individual reference arm 310, and a corresponding reference mirror 320. Each OCT subsystem of the n constituent OCT subsystems of the OCT probe is individually configured to attain an individualized OCT scans independent of the other constituent OCT subsystems. More specifically, the parameters of each of the elements of the n OCT constituent subsystems may be adjusted independently of the others. For example, in an embodiment, the wavelength range of a light source 300 of any of the n constituent OCT subsystems may be substituted for one that differs from its neighboring subsystem and may be adjusted to configure, e.g., optimize, the constituent OCT subsystems scan for a particular type of tissue 270. In yet another embodiment, the distance between the reference mirror 320 of any of the n constituent OCT subsystems and its corresponding reference arm 310 may be adjusted to optimize that constituent OCT subsystems scan for a particular depth or wavelength of illumination.

Still referring to FIG. 3, OCT systems have two fundamental operational modes: the first fundamental operational mode comprising Time Domain Optical Coherence Tomography (TDOCT) and the second fundamental operational mode comprising Fourier Domain Optical Coherence Tomography (FDOCT). Both of these modes of operation are integrable with the OCT probe arrangement. The FDOCT may also be split into two types of implementation: the first implementation being Spectral Domain Optical Coherence Tomography (SDOCT) and the second implementation being Swept Source Optical Coherence Tomography (SSOCT). Although both systems are implemented on the same basic principle approach they differ in application. Specifically SDOCT employs a broadband illumination source and a spectrometer based detector, whereas SSOCT employs a swept source illumination source and a broadband photodetector. Both systems will be described in greater detail below with respect to integrating them within the OCT probe system.

Still referring to FIG. 3, an SDOCT system functions by illuminating the sample with a broadband interrogating illumination (typical bandwidth of ≈100 nm). This illumination interacts with the sample through a combination of transmission, absorption, scattering, and reflection phenomena. A proportion of this interrogating illumination is returned to the sample arm optical terminal and directed through fiber optic channels (or an equivalent) to an interferometer. The interferometer then combines this signal with the reference signal reflected from the reference mirror and channels the combined signal to a spectrometer which includes, in general, a grating to separate light into the different wavelength spatially, and a camera for detection, for example a CCD (charge coupled devices) or CMOS camera. The intensity at each wavelength forms a distribution that is spatially encoded with information regarding the amount of illumination that returns from varying depths through the tissue along the scan axis. A Fourier transform may then be applied to this signal to decode the spatial information and determine the amount of return illumination which is reflected from the varying depths.

Still referring to FIG. 3, to integrate an SDOCT mode of operation into the OCT probe arrangement, at least one of the n constituent OCT subsystems can have elements which facilitate SDOCT. In some embodiments, the SDOCT arrangement may have the same form as the example OCT system, as shown in FIG. 1, with substantially the same elements. To enable the OCT probe to perform SDOCT, the elements may be adjusted to meet the following criteria. In order for any of the n constituent OCT subsystems to perform an SDOCT scan, their elements can be configured as follows. Firstly, the illumination source 300 is configured to have properties such that it outputs broadband low coherence illumination. For example, a super luminescent diode (SLD) having a center wavelength of 1310 nm, a coherence length of 15 mm and a bandwidth of 100 nm can be used for OCT.

Still referring to FIG. 3, in implementations, especially those involving fiber optic delivery, the components of OCT systems, including SDOCT, SSOCT, TDOCT, or any other applicable OCT arrangement, such as the interferometer, the fiber optics, the detector, the reference mirror, and any other applicable elements, may be configured or customized for a particular wavelength band (usually determined by the specific wavelength band emitted by the chosen light source 300). This is due to the practical limitation of the designs in each of the optical components. Thus, the interferometer 350, the fiber optics 335, the detector 340, and the reference mirror 320, of the at least one of the n constituent OCT subsystems may have optical components chosen to facilitate the specific wavelength band emitted by the light source 300. More specifically, in order to employ this wavelength band, the fiber optic elements 335 used to transfer the illumination throughout the constituent OCT subsystem may be chosen such that the loss of the optical elements are sufficiently low to allow enough propagation of this specific broadband illumination.

Still referring to FIG. 3, for example, a fiber optic cable, having a cutoff wavelength of 1200.+−0.70 nm and insertion loss less than 0.5 dB, could be used for a light source emitting a broadband illumination of operating wavelength of 1270 nm-1625 nm with center wavelength around 1310 nm. In addition, the optical properties of the interferometer element 350 are chosen to allow for the coupling and splitting of illumination signals at this bandwidth illumination. For example, a 2×2 fiber coupler having an operation band between 1200+/−70 nm is optimized for a laser operating at 1200+/−70 nm and is ideal for OCT image. For detection, a silicon-based spectrometer, for example, would be applicable for a light source emitting a broadband illumination of between 190 nm to 1100 nm. In addition to the spectrometer, a camera, for example, a CCD (charge coupled devices) or CMOS camera, is used to detect the chosen wavelength range. The aforementioned wavelength and wavelength ranges are given as examples only and are not to be construed as limiting embodiments of the OCT probe system as herein described. The wavelength and wavelength ranges described may be adjusted for the particular application of the OCT probe as herein disclosed by configuration adjustments.

Figure 4A:
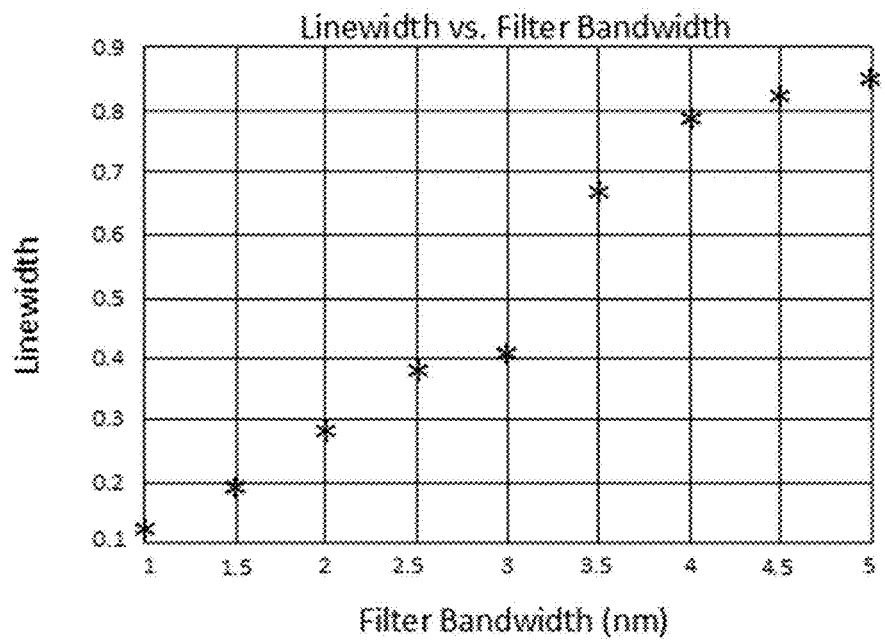
FIG. 4A is a diagram illustrating the instantaneous linewidth of a swept source laser.
Figure 4B:
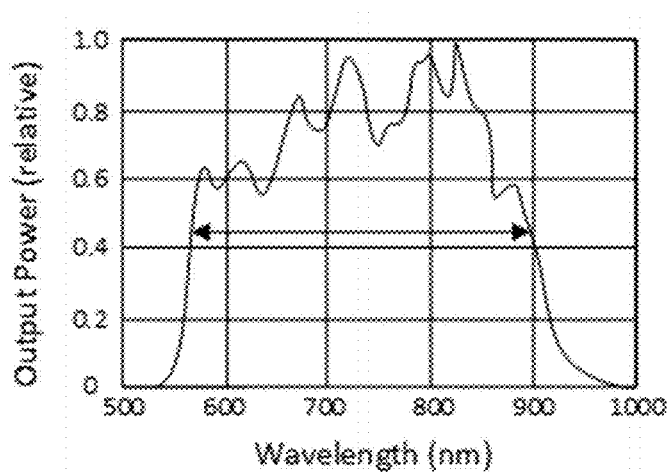
FIG. 4B is a diagram illustrating a general distribution of a broadband illumination used in SD-OCT.

Referring to FIGS. 4A and 4B, these diagrams respectively illustrate the instantaneous linewidth of a swept source laser and a general distribution of a broadband illumination used in SD-OCT. A system configured to acquire SSOCT scans functions in substantially the same way as an SDOCT system in that the raw detected signal to be processed is the same, essentially being a distribution of signal strengths for each wavelength. Although the acquired signal and its subsequent processing to decipher its encoded spatial information is essentially the same the main difference lies in the manner in which this signal is acquired. Whereas an SDOCT scan uses a broadband illumination source and a spectrometer, a SSOCT scan uses a narrow band swept illumination source and a simple photodetector capable of detecting all of the narrow bands swept through by the source. The difference in source illumination is highlighted in FIGS. 4A and 4B where FIG. 4A shows an example instantaneous linewidth of a sweep source laser; and FIG. 4B shows an exemplary distribution of a broadband illumination used in SD-OCT. The swept narrowband illumination source generally functions by sweeping through a range of wavelengths (for example the range of wavelengths ranging from 1260 nm to 1360 nm). An example of such a swept illumination source would be MEMS based swept source [Conf Proc IEEE Eng Med Biol Soc. 2011; 2011:6134-7. doi: 10.1109/IEMBS.2011.6091515.] which gives a sweeping frequency of .about.23 kHz, as an example, with a center wavelength of 1330 nm and a sweeping range of approximately 100 nm. Since the swept source laser outputs a narrow band of light that sweeps across a range of frequencies, the light intensities detected by the photodetector as a function of time become a spectrum which corresponds to light reflected and interfered at different wavelengths.

Referring back to FIG. 3, with respect to an OCT subsystem, at any given time t the light source 300, being a swept narrow band illumination source, is emitting a narrowband interrogating illumination into the interferometer. At this same time t the interference signal being acquired by the detector 340 in this case being a photodetector with properties configured specifically for detecting the illumination in the range of the swept illumination source corresponds to the sample's response to the particular wavelength being emitted by the narrow band swept illumination source. For example, a silicon photodetector is suitable for detecting light in the wavelength range of 200 nm-1100 nm while an indium gallium arsenide (InGaAs) photodetector has high photosensitivity in the near-infrared (NIR) range between 800 nm-1700 nm. Thus, by detecting the signals as a function of time with respect to sweeping rate of the swept source, a similar spectrum to that employed by SDOCT system is acquired by an SSOCT system. Similar to the elements used to acquire an SDOCT scan, the elements of an OCT system used to acquire an SSOCT scan comprise optical components that are customized for particular wavelength band of illumination, usually determined by the wavelength band emitted by the chosen light source 300 in this case a swept narrowband illumination source having a particular range of wavelengths.

Referring back to FIG. 2, in the example embodiment of a PS-OCT system, a computer controlled frequency sweeping laser source, e.g., swept source laser, outputs an illumination beam such as that used in the SSOCT system. This illumination beam passes through a polarizer to create linearly polarized illumination which subsequently passes through a non-polarizing beam splitter that splits the power of the input light equally into two arms—a reference arm at the bottom and a sample arm to the right. The light in the sample arm passes through a quarter-wave plate at an angle of approximately 45 degrees which sets the light to a circular polarization state going into the tissue sample. This circularly polarized light scans across a region in the sample to generate an image through a set of scanning mirrors or galvanometers that are computer-controlled through motor controllers. Although included in this example, a scanning mechanism may not be included when employing a PSOCT system, such as shown in FIG. 2, as a constituent OCT system to be used in the OCT probe. Light reflected and scattered from the tissue sample travels to the quarter-wave plate and is subsequently coupled into two orthogonal channels in the polarization maintaining fibers, each channel supporting the propagation of linearly polarized light towards the non-polarizing beam splitter.

Still referring back to FIG. 2, the light in the reference arm travels to the non-polarizing beam splitter after passing through optical components. These components include a collimator, a quarter-wave plate at an angle of approximately 22.5 degrees, a dispersion compensation unit, an iris, and/or a neutral density filter. The quarter-wave plate splits the reference arm power equally between the two orthogonally polarized channels while the dispersion compensation unit, the iris, and the neutral density filter maximize the signal-to-noise of the interferometric signal.

Still referring back to FIG. 2, the non-polarizing beam splitter then combines the reflected reference light beam and the reflected and back-scattered sample light beam. The combined interferometric signal then propagates to the top to another non-polarizing beam splitter that splits the power equally into two orthogonal directions. Each of the split powers goes through a polarizing beam splitter that splits the interferometric signal into two orthogonal polarization channels. The same two orthogonal polarization channels from the two polarizing beam splitters then propagates the interferometric signals to a balanced detector for converting the interferometric signals into electrical analog signals. These electrical analog signals are then converted to digital signals through a data acquisition card (DAQ) which is then stored and processed in the connected computer to generate PSOCT images in this particular example.

Referring back to FIG. 3, in the system, each individual sample arm 330 comprises an individual fiber optic component 500 (or equivalent) embedded or constructed either in its entirety or partially within the probe head 305 at a desired static spatial orientation. Each of these individual fiber optic components acquires an A-scan rectilinear with its light path direction providing an effectively one-dimensional OCT image along said direction.

Still referring back to FIG. 3, in some embodiments, a processor may amalgamate the optical coherence tomography image dataset of A-scans into a single OCT image (visualization). This may be accomplished by stitching the A-scans into a common image space, wherein the individual's A-scan projections in the image space are dependent on the spatial orientation of the individual fiber optics from which they were acquired. This knowledge of the positions and orientations of the external beam paths can therefore be employed to generate, based on the A-scans, a composite volumetric image. In some embodiments, the A-scans may overlap in the image space, in such a case further processing may be executed as described below to clarify the particular regions where this occurs. In some cases, this may be a desirable result as more data about the overlapped region is available which may potentially provide a more accurate representation of the region also below described in further detail. In one example implementation, the image data from the multiple A-scans is spatially interpolated when generating the composite volumetric image.

Referring to FIG. 5A and referring back to FIG. 3, the diagram of FIG. 5A illustrates multiple example configurations of the sample arm fiber optic components in the probe head 305 of the OCT probe, as shown in FIG. 3, in accordance with embodiment of the present disclosure. Each example configuration is illustrated as a cross-sectional view of the probe head 305, which, in the example embodiments shown, are of a cylindrical shape. In the example embodiments shown, each probe head 305 contains fiber optic components of the n sample arms from the n constituent OCT subsystems. Each sample arm 330 has a respective fiber optic component 500 located within the probe head 305, aligned statically relative to the other n−1 fiber optic components belonging to the other n−1 sample arms 330. Each fiber optic component has an optical terminal at the outer boundary of the probe head 305, for example as shown as 505 in FIG. 5A. This optical terminal may act as both an optical output, whereby it outputs the interrogating illumination transmitted from a light source 300 onto the sample 170, and an illumination collector whereby it guides any return illumination from the sample 170, back into its fiber optic component to be transmitted to the corresponding sample arm 330 of its constituent OCT subsystem. The interrogation and return illumination are subsequently combined and their interference signal used to form A-scans rectilinear with the light path of the interrogating and reflected illumination providing a substantially one dimensional OCT image along said path. These light paths (external beam paths), linear light paths 510, as shown in FIG. 5A, are defined by the direction in which the illumination propagates within the fiber optic components 500 after entering and before exiting the optical terminal. Thus, any acquired OCT A-scans would be acquired along the linear light paths 510, as shown in FIG. 5A.

Still referring back to FIG. 5A, the optical terminal mentioned above may include one or more polarization optics, lenses, and/or collimators that are provided to interrogate the sample with a specific spot size, resolution and polarization state. In some embodiments, the optical terminal may include a GRIN lens that is used to alter the direction of the light upon exiting and entering the probe head 305.

Figure 5B:
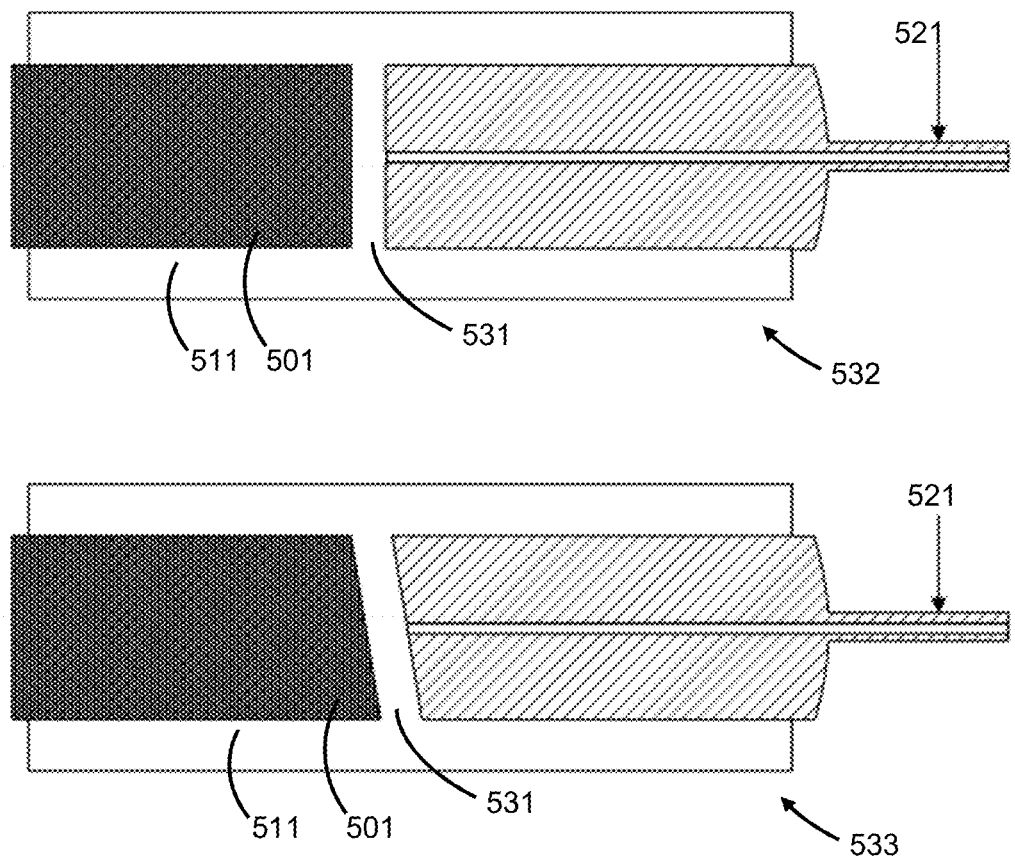
FIG. 5B is a diagram illustrating an example OCT probe head with graded index (GRIN) lenses.

Referring to FIG. 5B, this diagram illustrates several different example OCT probe designs have been realized using different optical elements, in accordance with embodiments of the present disclosure. In one example configuration, an optical terminal comprises a graded index (GRIN) lens, as shown in FIG. 5B, used for collimating light output at the fiber. The GRIN lens 501 can be attached to the end of a fiber optic 521 through a ferrule and a matting sleeve 511. This GRIN lens surface can be made at an angle 531 of approximately 0 degree with respect to the fiber facet or at an angle 541 of approximately 8 degrees to the fiber facet to minimize OCT image artifacts from surface reflection of the optical elements. An anti-reflective coating at the lens surfaces can also be added to further minimize surface reflections. If the probe size is to be larger, a typical fiber collimator with multiple lenses (for aberration correction) can be used instead of a GRIN lens. These collimators can be easily attached to a fiber through typical fiber connectors. If the light is desired to be focused at an angle other than straight forward from the fiber output, a prism can be placed in front of the GRIN lens or a collimator to direct the light beam to a different angle. Polarization optics, such as a quarter waveplate, can also be used if a selected polarization output is required.

Still referring to FIG. 5B, an extension of the GRIN lens configuration has been demonstrated through using two GRIN lens as described in the paper by Wu, Jigang, et al. "Paired-angle-rotation scanning optical coherence tomography forward-imaging probe," Optics Letters 31.9 (2006): 1265-1267. By rotating two angled GRIN lens that are placed at the output of the fiber optics, the light output beam can be collimated and focused at a location with an angle that is different with respect to the forward direction of the light output from the optic fiber. Such a configuration enables the scanning mechanism, for example a motor or a galvanometer, to be mounted away from the tip of the fiber probe to enable a small probe tip while enabling the light beam to be directed at different location of the samples.

Still referring to FIG. 5B, in another configuration, a spherical ball lens could be used in the place of a GRIN lens to collimate and focus the light output from the optic fiber. An example is described in the paper by Singh, Kanwarpal, Daisuke Yamada, and Guillermo Tearney. "Common Path Side Viewing Monolithic Ball Lens Probe for Optical Coherence Tomography," Medical Technologies in Medicine/Sovremennye Tehnologii v Medicine 7.1 (2015). The advantage of using a ball lens is that the entire probe could be made monolithic. The cost of the probe can be potentially cheaper compared to the GRIN lens.

Referring to FIGS. 5A and 5B, the individual placement of fiber optic components in the probe head 305 relative to one another allows for the formation of A-scan acquisition arrays that may be used to define specific volumetric regions of OCT imaging. In some array configurations it may be advantageous to alter the direction of interrogation at the end of the fibers by using an optical lens. In one configuration, a graded index (GRIN) lens is used for collimating light output at the fiber. For example, as shown in FIG. 5B, a GRIN lens 501 can be attached to the end of a fiber optics through a ferrule 531 and a matting sleeve 511. This GRIN lens surface can be made at an angle of approximately 0 degree with respect to the fiber facet of the fiber optic 521, such as element 532, as shown in FIG. 5B, or an angle to the fiber facet of the fiber optic 521, such as shown as element 533, to minimize OCT image artifacts from surface reflection of the optical elements.

Still referring to FIGS. 5A and 5B, an anti-reflective coating at the lens surfaces can also be added to further minimize surface reflections. If the probe size is made larger, a typical fiber collimator with multiple lenses (for aberration correction) may be used in place of a GRIN lens. In general, these collimators are easily attached to a fiber through typical fiber connectors. If it is desired that the interrogation beam be focused at an angle other than straight forward from the fiber output, a prism or collimator may be placed in front of the GRIN lens to direct the light beam at a different angle. Furthermore an extension of the GRIN lens has been demonstrated through using two GRIN lens. This GRIN lens configuration is incorporated by rotating two angled GRIN lenses at the output of the fiber optic. Using this configuration the light output beam may be collimated and focused at a different angle with respect to the forward direction of the light output from the optical fiber.

Still referring to FIGS. 5A and 5B, in the case where a rotation motor is used this implementation allows it to be mounted away from the tip of the fiber probe facilitating a smaller probe tip design while enabling the light beam to be directed at different location of the samples. In yet another configuration, a spherical ball lens could be used in place of a GRIN lens to collimate and focus the light output from the optic fiber. The advantage of using a ball lens is that the entire probe may be made monolithic. Leading to a potentially reduced cost probe in comparison to one constructed with a GRIN lens design. In yet another alternate embodiment polarization optics, such as quarter-wave plates, may also be used in the configuration if a selected polarization output is required.

Figure 5C:
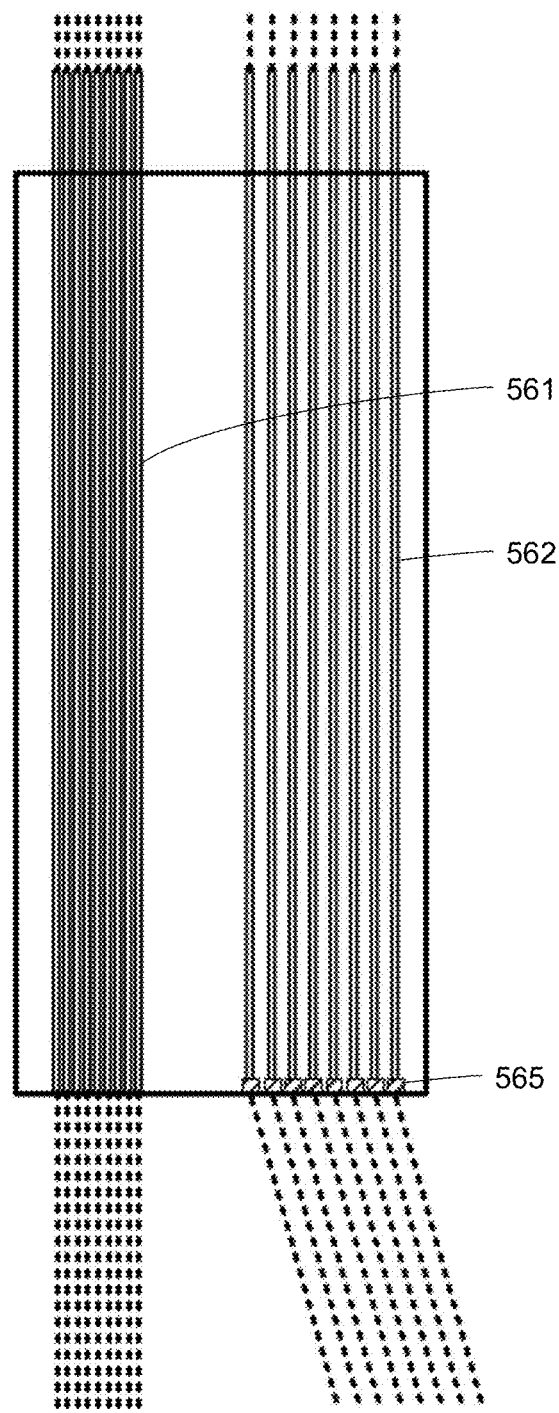
FIG. 5C is a diagram illustrating an elevated view of an example OCT probe head employing distal GRIN lenses.
Figure 5D:
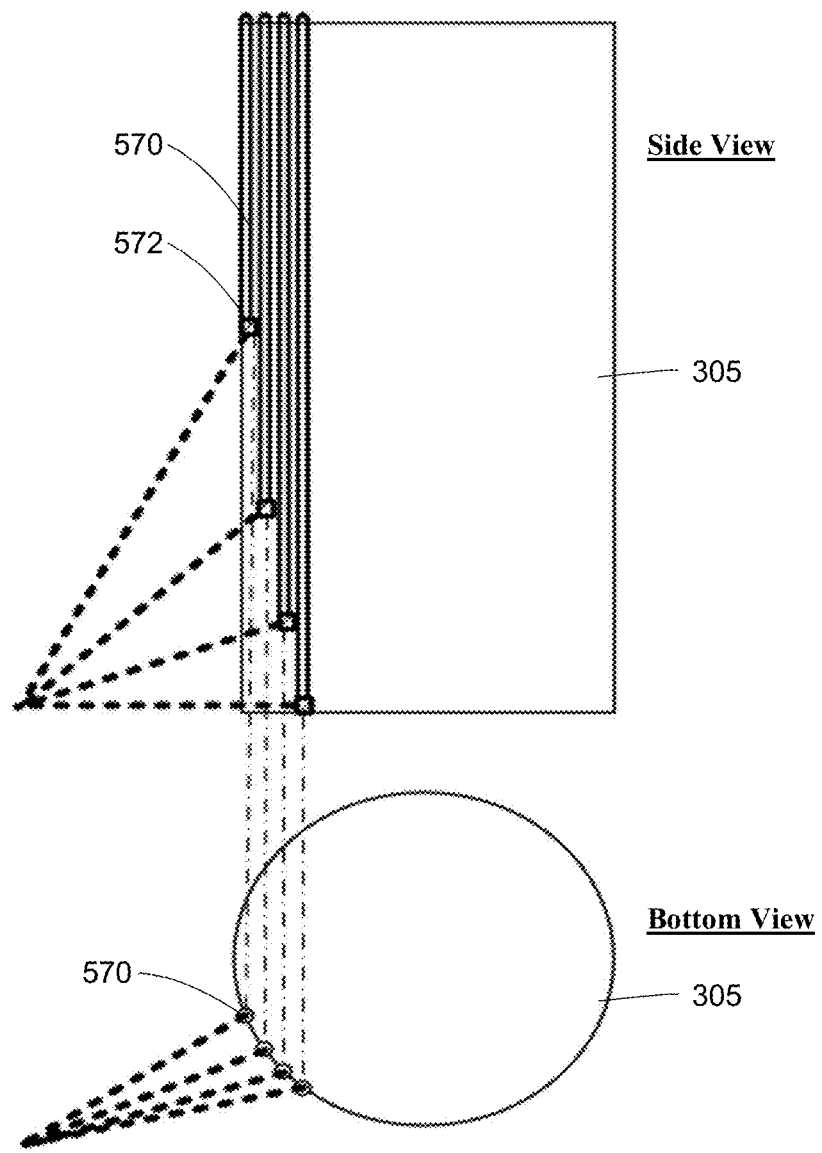
FIG. 5D is a diagram illustrating an example OCT probe head with distal mirrors and lenses
Figure 5E:
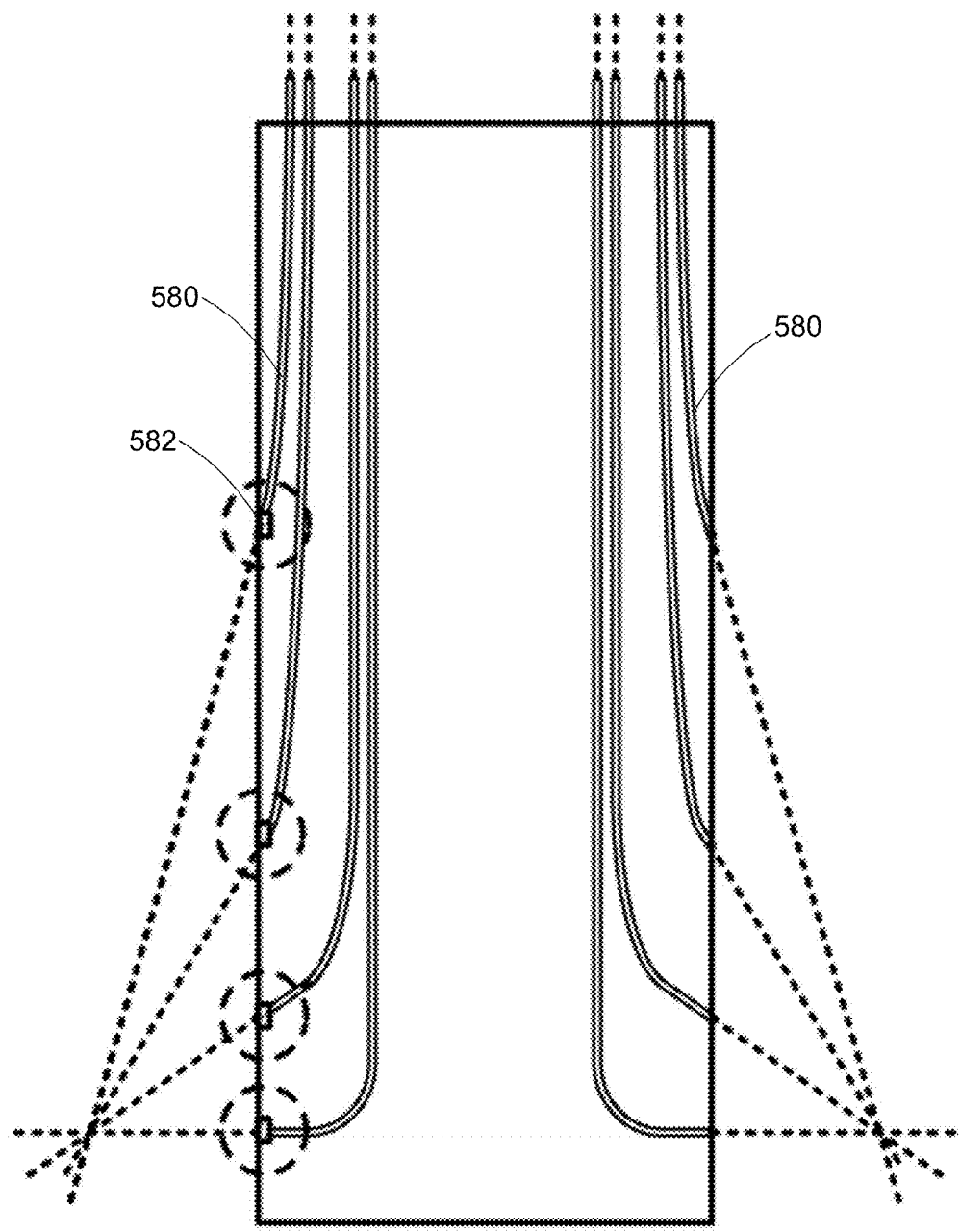
FIG. 5E is a diagram illustrating an example OCT probe head with curved optical fibers housed within the probe head, where distal collimation optics are employed to collimate an optical beam emerging from the optical fibers.
Figure 5F:
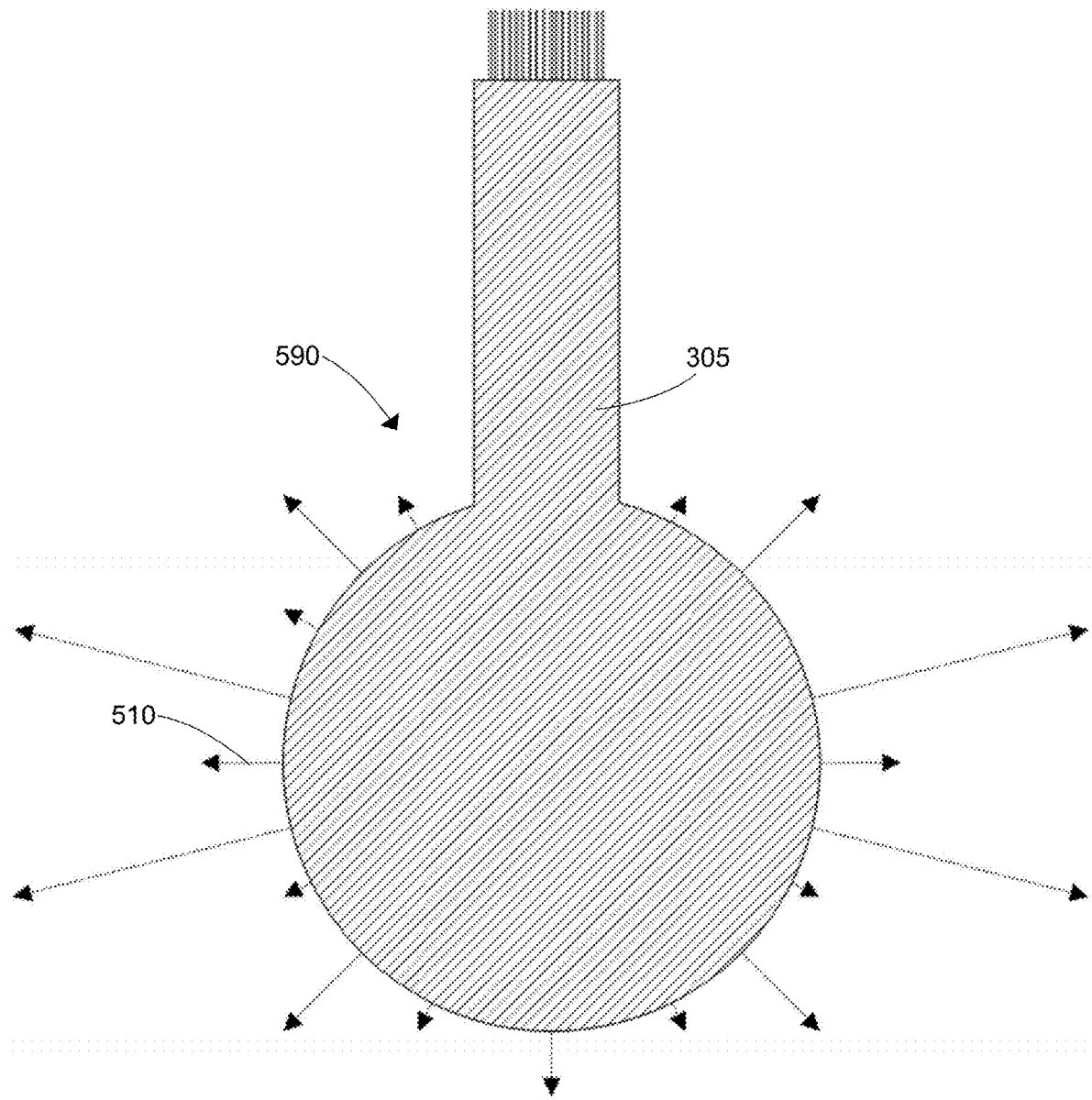
FIG. 5F is a diagram illustrating an example OCT probe head configured to provide a spherical distribution of OCT interrogation A-scans for achieving a larger field-of-view and angle-of-view.

Referring to FIGS. 5C-5E, together, these diagrams illustrate cross-sectional views of other internal configurations that may be used to form the probe heads, as shown in FIG. 5A, in accordance with embodiments of the present disclosure. For example, the diagram of FIG. 5C illustrates an internal cross-sectional view of probe head 540 from FIG. 5A. The array of fibers providing direct imaging 561 may be configured for imaging at an angle of approximately 0 degree from the axis of the probe head while the adjacent array of fibers 562 may be configured for imaging on an angle defined by the use of the GRIN lenses 565. In an alternate implementation, as shown in FIG. 5D, OCT acquisition fibers 570 may be embedded in grooves along the outer surface of a probe head 305 and optically connected with micro sized mirrors or lenses 572 to change the interrogation angle of the light. In a yet another alternate implementation, the diagram of FIG. 5E illustrates an internal cross-sectional view of a probe head 580, as shown in FIG. 5A. The fibers 580, in this implementation, are curved to guide the interrogation light to the desired angle. Also shown in the figure are collimation optics 582 that may be used to boost performance of the OCT acquisition fiber. In a further embodiment, the OCT acquisition fibers may be oriented such that they form a sphere like shape and may be used to interrogate a tissue such as an organ internally where the interrogation pattern is sphere like in its propagation. For example, such a probe is shown in FIG. 5F where the probe head 590 has a spherical distribution of OCT interrogation A-scans 510 for achieving a larger field-of-view and angle-of-view.

Figure 6:
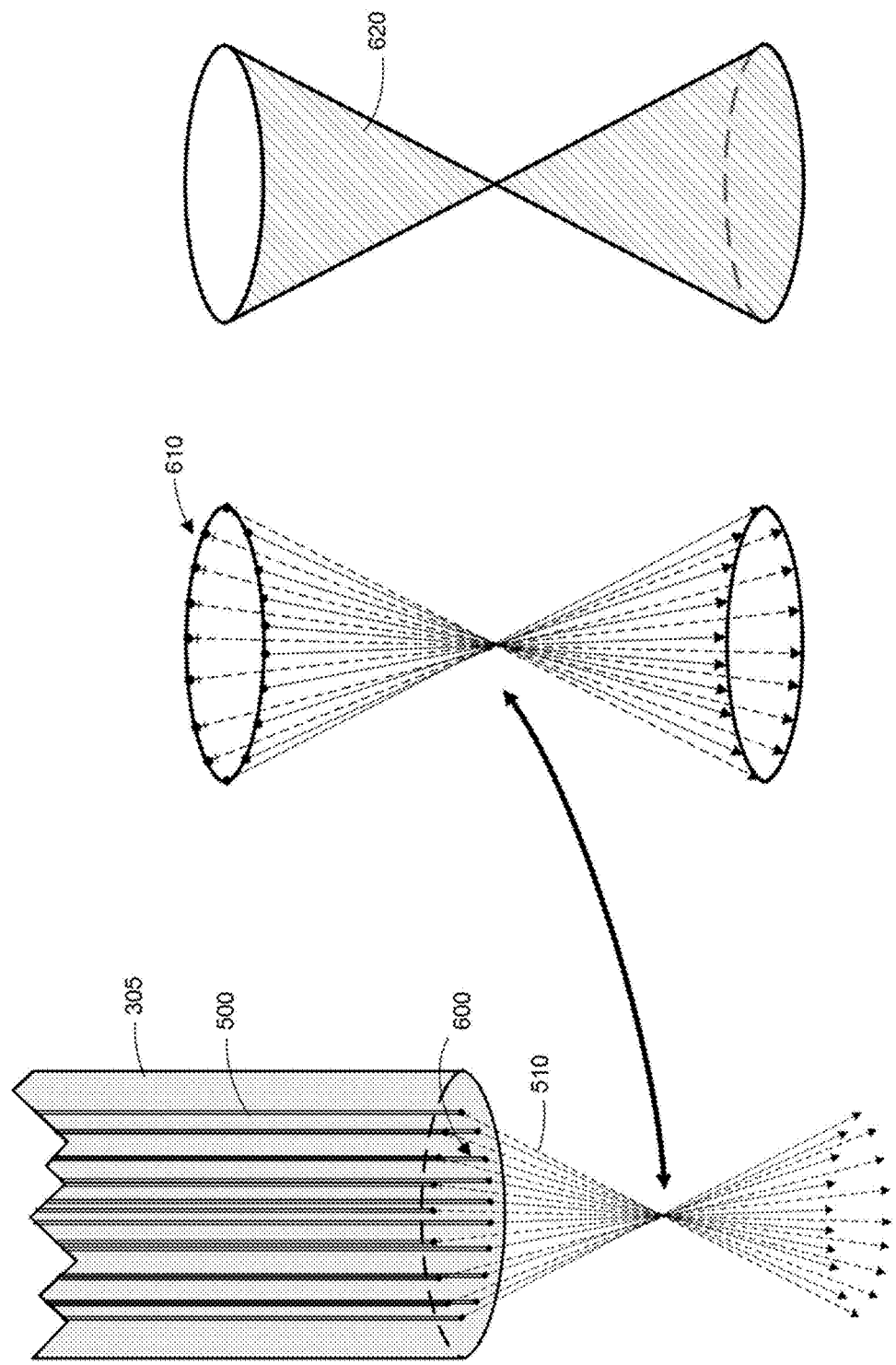
FIG. 6 is a diagram illustrating an example OCT probe head having an array of optical fibers configured to emit a plurality of optical beams in a cone-shaped array.

Referring to FIG. 6, this diagram illustrates an example A-scan acquisition array with a conical surface-like volumetric region of OCT imaging, in accordance with an embodiment of the present disclosure. The acquisition array 600 embedded in the probe head 305 contains multiple fiber optic components 500 angled inwards at a common angle in an annular arrangement such that the acquired A-scans 510 form a conical shape as shown by the diagram 610. Thus the OCT imaging acquired by the acquisition array 600 would be in the form of a volumetric region which emulates a conical surface such as that shown by the diagram 620. Although the multiple fiber optic components 500 are angled inwardly in a common annular arrangement to facilitate a conical configuration of A-scans, the multiple fiber optic components 500 may, alternatively, be directed outwardly in a common annular arrangement to facilitate a conical configuration of A-scans. The example annular configuration shown in FIG. 6 is but one example of an arrangement of the multiple fiber optical components 500; and, in other example embodiments, the multiple fiber optical components need not be configured in an annular configuration.

Figure 7:
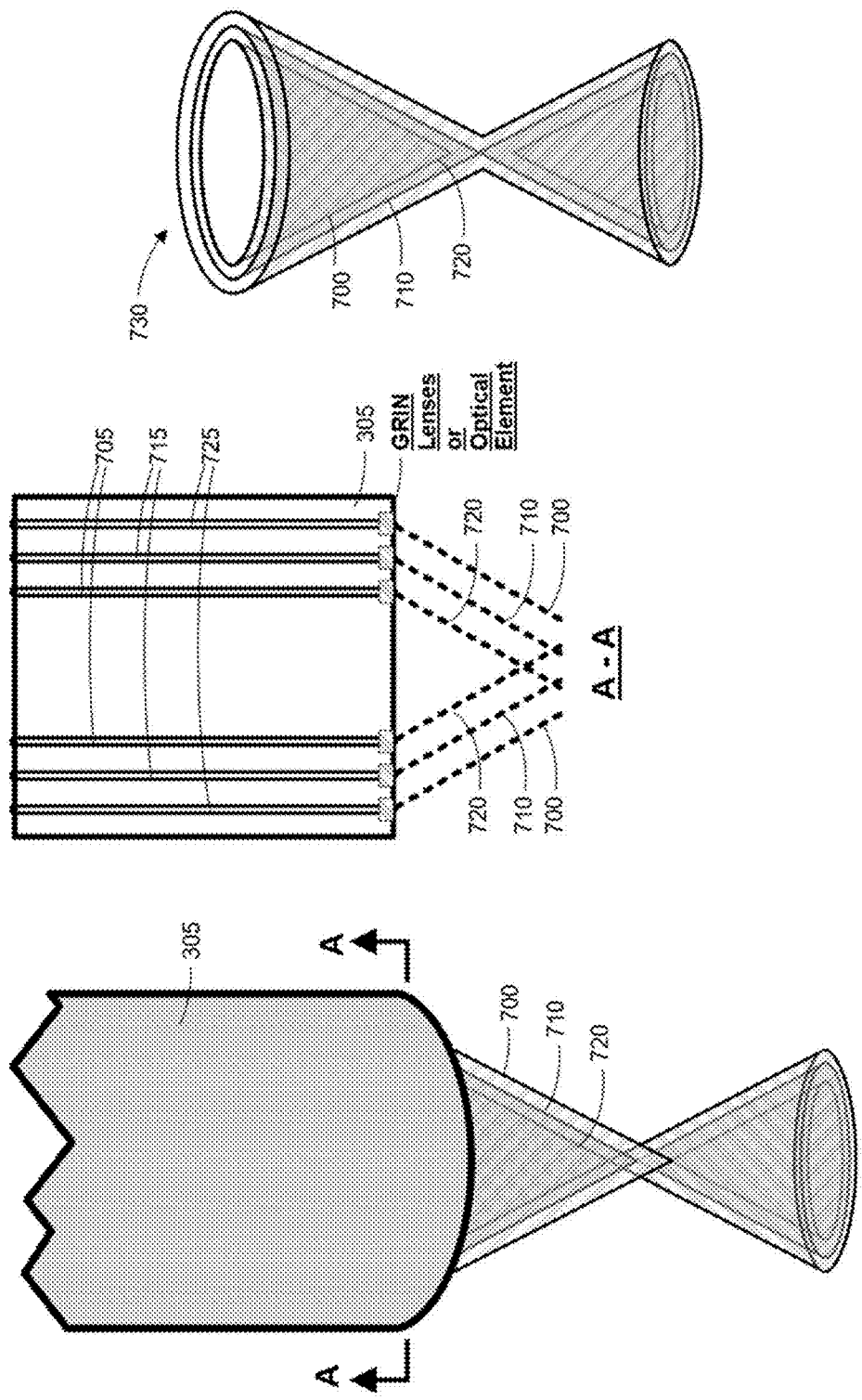
FIG. 7 is a diagram illustrating an example OCT probe head having a plurality of arrays of optical fibers configured to emit optical beams in a plurality of cone-shaped arrays.

Still referring to FIG. 6, furthermore, the acquisition array 600 may be replicated in a repeating concentric manner to form an A-scan acquisition array which acquires OCT imaging in a conical volume, e.g., not a surface volume. An example of such a configuration is shown in FIG. 7, where the probe head 305 contains three annular arrays 705, 715, and 725 of fiber optic components angled inwards at a common angle enabling them to acquire three adjacent emulated conical surface volumetric regions 700, 710, and 720 of OCT imaging. By combining these conical surface images, an effective three dimensional imaging volume may be formed such as that shown at 730 in FIG. 7, potentially providing further information benefitting the user.

Still referring to FIG. 6, although the examples involve a cylindrical probe head acquiring a conical surface volume or conical volume, that any applicable shape of probe head, surface volume, and volume may be acquired. Examples of such being a rectangular prism-shaped probe head and a rectangular prism-shaped probe head e.g., for acquiring a rectangular surface, a planar surface, a cubic volume, a rectangular prism-shaped volume, etc.

Still referring to FIG. 6, as above mentioned, the configuration of the example OCT probes, as disclosed herein, allows the user to individually configure the elements of the probe. In one example embodiment, the parameters or type of the light source elements 300 of each of the n constituent OCT subsystems may be altered such that they are optimized for imaging tissue.

Still referring to FIG. 6, presently, the effectiveness of OCT (SDOCT, SSOCT, TDOCT, PSOCT, etc.) imaging of tissues at subsurface levels is highly dependent on the center wavelength and bandwidth chosen for the interrogation. The effectiveness is dependent on the interrogating illuminations' ability to penetrate the surface of the tissue, interact with its molecular structure and return to the detector with a high enough interference signal to form OCT images with meaningful resolution. For example, absorption spectra are relatively high for hemoglobin (and deoxyhemoglobin) for wavelengths below .apprxeq.700 nm, and for water for wavelengths above .apprxeq.950 nm, both of which form a substantial proportion of almost all tissue but can vary between types. Providing illumination light, having a wavelength that penetrates as deep into the tissue as possible, while still providing significant return illumination to form a resolved OCT image is beneficial.

Figure 8:
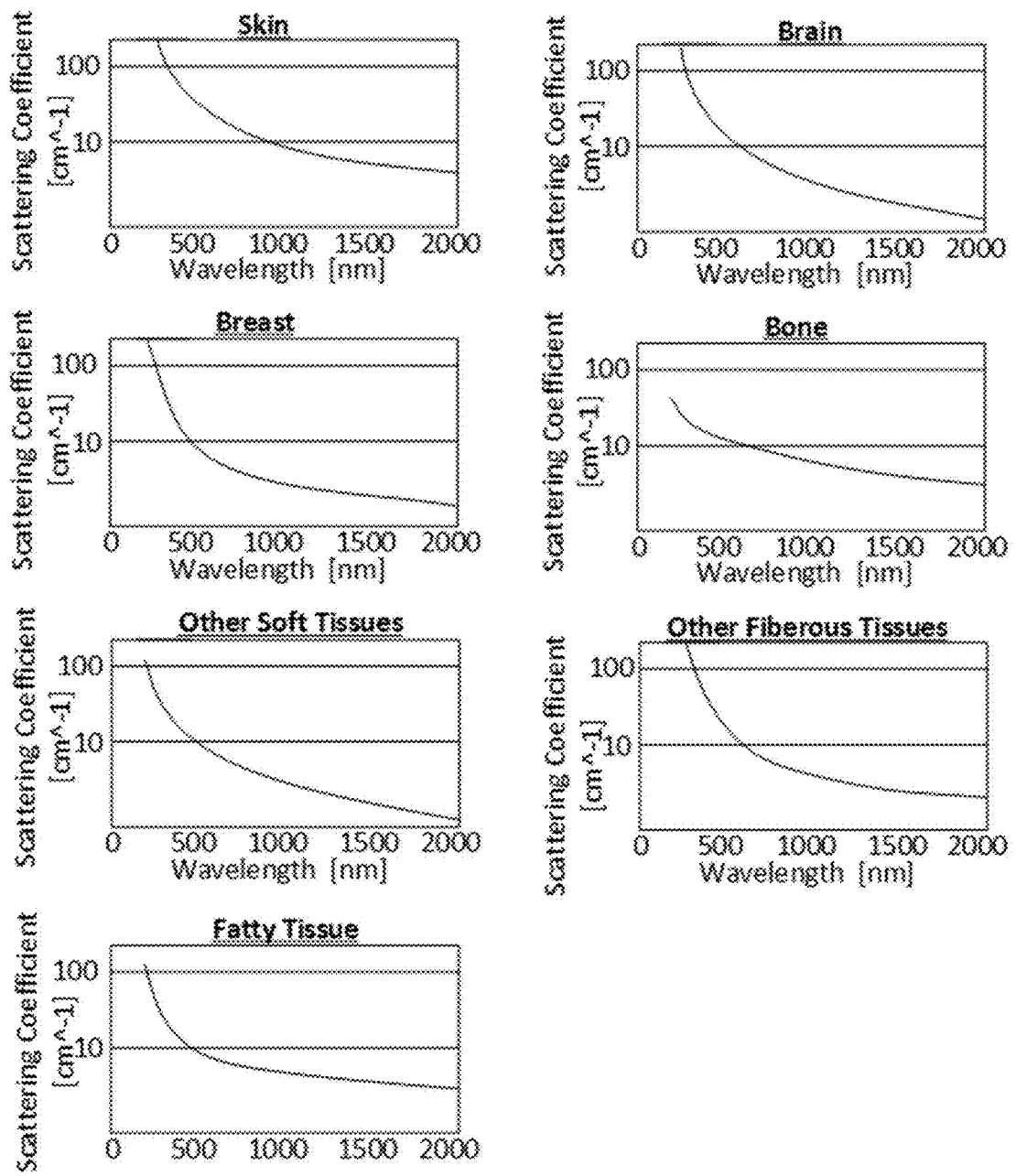
FIG. 8 is a diagram illustrating various scattering coefficients for different types of tissue.
Figure 9:
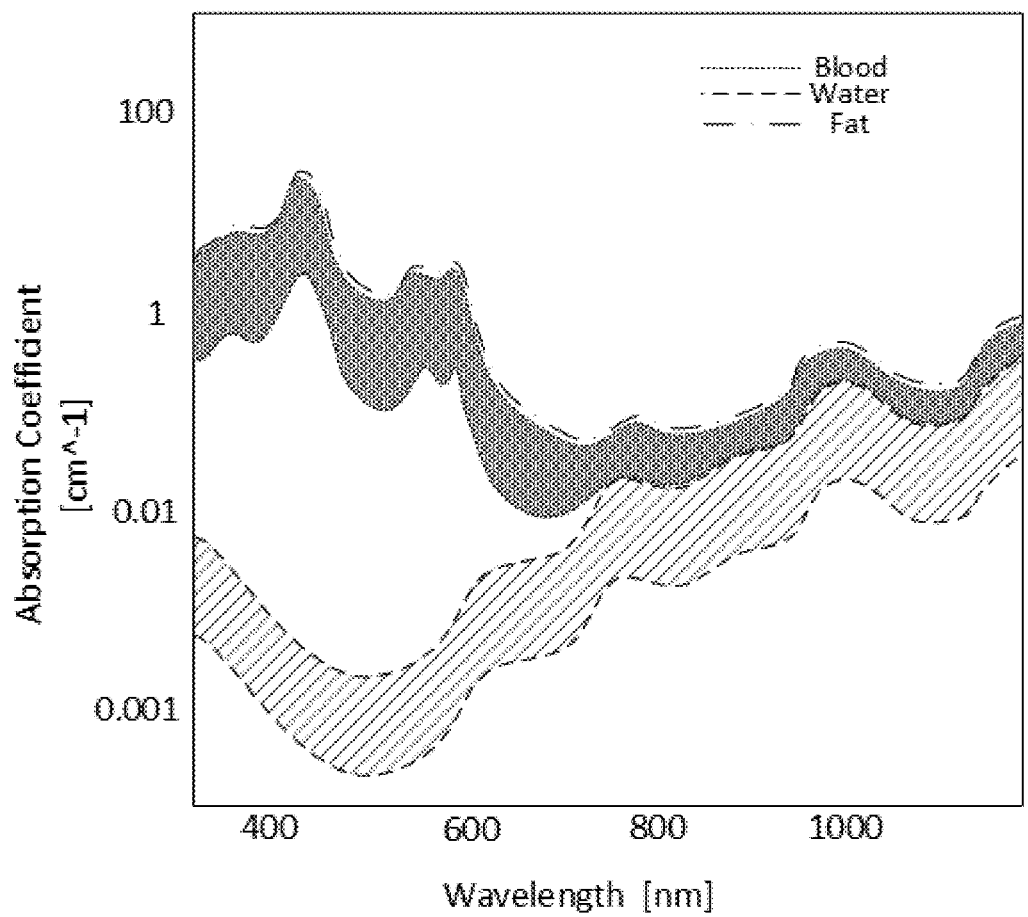
FIG. 9 is a diagram illustrating various absorption spectra for different types of anatomical component molecules.
Figure 10A:
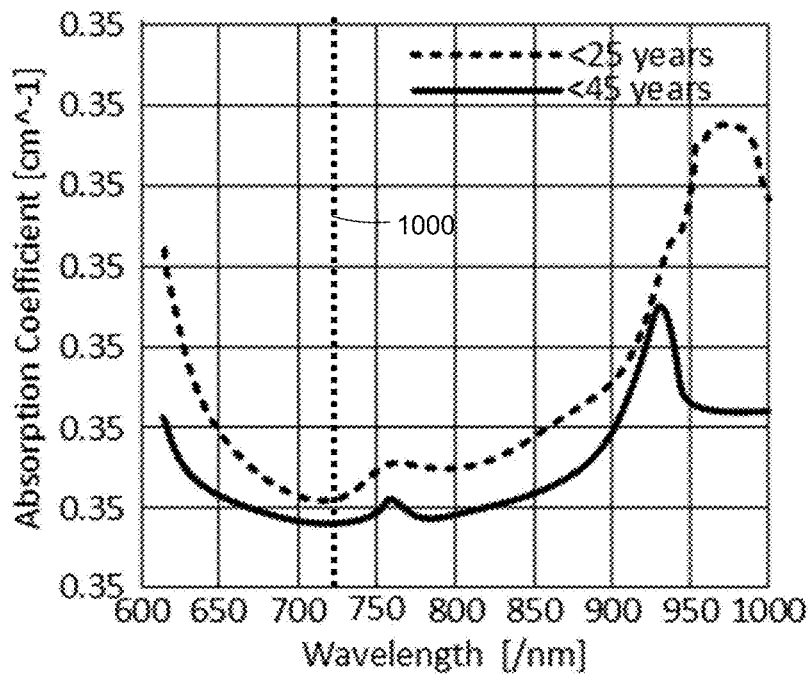
FIGS. 10A and 10B are diagrams, together, illustrating absorption spectra for different types of breast and penetration depth for various types of anatomical tissues.
Figure 10B:
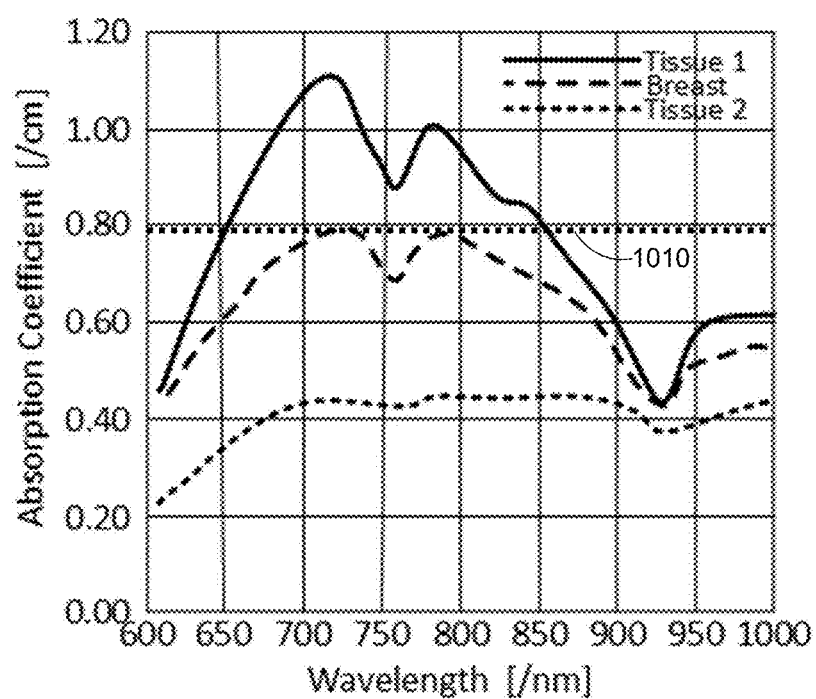

Still referring to FIG. 6, and referring ahead to FIGS. 8 and 9, in order to determine the wavelength that best approximates this situation, the optical properties of the tissue should be taken into consideration, in accordance with an embodiment of the present disclosure. These optical properties may be determined from scientific analysis and indeed the literature provides many such papers outlining the relevant information. One such paper is provided by Jacques, Steven L. "Optical properties of biological tissues: a review," Physics in medicine and biology 58.11 (2013): R37. in which the optical properties of tissue varying between subject and between tissue type are modelled and the data provided. For example, as shown in FIG. 8 the plots provide exemplary dependencies of the optical scattering coefficients of tissue on incident illumination wavelength for various types of tissue. Similar to FIGS. 8 and 9 is a graph illustrating a plot of the exemplary dependence of the optical absorption coefficient on incident illumination wavelength for the various predominant light absorbers in the majority of tissues. Where the patterned sections are specific ranges within which the curves are usually found.

Still referring to FIG. 6, and referring ahead to FIGS. 8 and 9, using these exemplary plots or those found in the paper by Jacques, Steven L. "Optical properties of biological tissues: a review," Physics in medicine and biology 58.11 (2013): R37 in addition to other available information it is possible to determine the center wavelength of an incident illumination that would maximize the penetration depth into a tissue of interest while still providing significant return illumination to form a resolved OCT image. Resultantly, the one or more of the light sources 300 of the n constituent OCT subsystems, contained within the OCT probe as disclosed herein, may be configured to emit illumination at this center wavelength allowing the interrogation A-scan parameters to be optimized for the tissue being scanned.

Referring to FIGS. 8, 9, 10A, and 10B, together, for example, if the OCT probe is being used to image a breast, one or more of the light sources 300 may be centered at a wavelength of 720 nm. This value can be arrived at by analyzing the scattering and absorption spectra of breast tissue from the example plots provided in FIG. 8 and FIG. 10A. The scattering coefficient of breast, like most tissues, decreases with increasing wavelength, thus the higher the wavelength the lower the likelihood of scattering. Although a lower scattering coefficient is desirable, a certain amount of scattering is required to provide a sufficient illumination return signal therefore it is not necessary to minimize this value in its entirety. The absorption coefficient of breast is minimized at a wavelength of 720 nm as can be seen from the line 1000 shown in FIG. 10A. Generally, the choice of wavelength of illumination for interrogation will be one that minimizes the sum of both the absorption and scattering coefficients to maximize the illumination return signal which seems to be the case at ≈720 nm. Thus, by configuring the illumination of the light source 300 to have a center wavelength at ≈720 nm, the penetration distance is maximized as can be seen from the line 1010 shown in FIG. 10B. The wavelength chosen in this example was for breast tissue and as such should not be taken as a limiting example in that wavelengths providing maximal or near maximal efficiency for other types of tissue when viewed by OCT imaging may be chosen as well. For the brain, wavelengths between 700 nm and 1800 nm may be suitable or preferable due to lower water absorption. Scattering is also lower at longer wavelength range providing a greater imaging depth potentially.

Referring to FIG. 7, in addition when forming a universal variant of an OCT probe as disclosed herein different sets of OCT arrays may be configured to have differing interrogation wavelength ranges for different tissues. For example, given the OCT probe illustrated in FIG. 7 each of the annular arrays may be optimized for a different tissue, for example, the distal array 705 may be optimized for imaging white matter, the middle array 715 may be optimized for imaging vasculature, while the proximal array 725 may be optimized for imaging muscle tissue. In another embodiment the OCT probe illustrated in FIG. 7 may have annular arrays optimized to view subtypes of a single organ such as the brain. For example, the distal array 705 may be optimized for imaging grey matter approximately 850 nm due to lower scattering and absorption in the human brain. The middle array 715 may be optimized for imaging human cranial bone at 1100 nm, again, due to the lower absorption and scattering coefficient for the human cranial bone. This configuration enables high quality OCT images can be obtained using the same probe.

Referring to FIG. 7 and referring back to FIG. 3, in addition to being able to configure the light source elements 300 of each of the n constituent OCT subsystems of the OCT probe, as disclosed herein, in some cases it may be advantageous to alter the reference mirror elements 320 of each of the n constituent OCT subsystems to optimize it for viewing the sample at a particular distance to the surface of the sample being scanned. More specifically the reference mirror is ideally located at a distance from the reference arm 310 such that the elapsed time taken by the illumination to travel to the reference mirror 320 and back to the reference arm 310 therefrom should be the same as the elapsed time taken by the illumination to travel from the sample arm 330 to the surface of the sample 170 and back to the sample arm 330. Given that different wavelengths of light travel at different speed through dispersive media such as air, liquid, or solid media. In order to ascertain the same elapsed time for each trip from the reference arm to the reference mirror and back and from the sample arm to the sample surface and back, the distance of the reference mirror from the reference arm may be configured (or optimized) to account for the speed of a particular wavelength of light in a specific medium described by the following equation: $v_\lambda = c/n_\lambda$, wherein $v_\lambda$ is the velocity of the light at wavelength $\lambda$, wherein c is the speed of light in a vacuum, and wherein $n_\lambda$ is the refractive index of a medium for a light at wavelength $\lambda$. Thus, the elapsed time taken for the reference trip relative to the sample trip must take into account these factors to be optimized.

Still referring to FIG. 7 and referring back to FIG. 3, for example, a first set of OCT subsystems interfaced with a first set of optical fibers of a multi-fiber OCT probe may be configured such that their respective reference arms are set such that the sensitivity is maximized within 500 um, in the axial direction, from a pre-selected external location (which may be a focal point). A second set of OCT subsystems interfaced with a second set of optical fibers of the multi-fiber OCT probe may be configured with reference arms set at a different location relative to the pre-selected external location, for example, such that the sensitivity is maximized 1 mm from the pre-selected external location, in a direction that is proximal to the probe. Similarly, a third set of OCT subsystems interfaced with a third set of optical fibers of the OCT probe may be configured such that their respective reference arms are set such that the sensitivity is maximized a 1 mm from the pre-selected external location, in a direction that is distal to the probe.

Still referring to FIG. 7 and referring back to FIG. 3, each set of optical fibers can have associated focusing elements, e.g., lenses, that focus the light emitted therefrom at different working distances, which improves the sensitivity of the imaging range they are focused on and at a different part of a stationary sample being imaged. Alternatively, every optical fiber of the probe can configured, by way of spatial positioning of the fibers and/or the selection of the associated focusing elements, to focus the light emitted therefrom at a common location.

Still referring to FIG. 7 and referring back to FIG. 3, in some example implementations, due to Fresnel reflection and the irregular contour of the sample, strong reflections, produced from the sample, may be directed in a direction that is different from the incident angle. In such a case, an OCT subsystem, interfaced with the optical probe, may be interfaced with two optical fibers, such that a first optical fiber of the optical probe is employed to direct incident light onto the sample and a second optical fiber is employed to collect reflected light. The second optical fiber of the multi-fiber probe may be oriented at an angle in which a strong reflected signal is expected to result based on light incident from the first optical fiber, provided the reference arm has an optical path length based on the round-trip delay through both the first and second fibers. For example, brain tissue is also a highly scattering tissue in which incident light can scatter within the tissue and exit the tissue surface at an angle that is different than the incident angle and the Fresnel reflection angle.

Still referring to FIG. 7 and referring back to FIG. 3, in one example embodiment, a multiple 1-D scanning probe is used to capture signals from different angles of the tissue and one of: display all signals from the different beam angles to the user, select the best data to display to the user, and combine data, e.g., weighted average the data, for display. Due to the optical path difference between the probe facet and the point, a different focusing optics might be used to focus the light onto the same common point.

Referring back to FIG. 3, similarly to the optimization of the choice of light source and reference arm, the interferometer 350, fiber optic channels 335, and detector 340 in the n constituent OCT systems may also be optimized. For example, specific parameters of each of the aforementioned elements (and any other applicable elements) may be chosen to provide the best efficiency with respect to illumination intensity conservation relative to the center wavelength or wavelength band chosen. Generally, the interferometer 350, detector 340, and fiber optics 335 may be configured based on the wavelength of illumination chosen, e.g., choosing the proper component that has an operation wavelength supporting the wavelength of interest. For example, interferometers that perform the action of splitting and combining light at a given ratio should be chosen specifically for the wavelength range of illumination they receive. To elaborate more specifically, an interferometer with an operating band between 1260 nm-1360 nm may be chosen for a laser excitation with the center wavelength of 1310 nm and bandwidth of 100 nm. For a sweep source laser with the center wavelength of 870 nm and bandwidth of 80 nm, an interferometer with an operating range between 790 nm and 950 nm is ideal.

Still referring back to FIG. 3, the choice of fiber optic cable element may be chosen to minimize optical losses when propagating through said element is also an important consideration when forming the OCT probe system disclosed herein, especially when acquiring a PSOCT scan. The choice of fiber optic cable in this case must have parameters specifically defined for the two orthogonal polarizations. Particularly when employing a PSOCT system a specific fiber optic cable might be used to preserve a particular polarization. For example, a "Panda" style polarization maintaining fiber or a "Bow-tie" style polarization maintaining fiber could be used to preserve two orthogonal linearly polarizing states. The choice of detector is an important consideration as well and may be optimized not only for the SSOCT and SDOCT scan type systems as described above but also varying wavelengths or additional features such as hyperspectral imaging, or overlapping acquisition arrays, and PSOCT imaging and various other imaging features of the OCT probe as further disclosed in this document.

Referring back to FIG. 5A, many of the configurations may have overlapping A-scans such as the configurations 520, 530, 550, 560, 570, 580, and 590 for example. These configurations may provide regions (or equivalently points) of greater scan accuracy. Wherein each of the overlapping regions have multiple data sets. Each data set may be acquired from multiple constituent OCT systems sample arms, wherein the acquired (effectively one-dimensional) OCT images overlap with the region. Depending on the acquisition parameters of the constituent OCT systems the multiple sets of data at the overlapped region or point may provide further beneficial information to the user.

Still referring back to FIG. 5A, in addition, if phase retardation imaging is performed, the "true birefringence," defined as the greatest birefringence value of the material here, and the direction of the optical axis can be more accurately measured in three-dimensional space through measuring the phase retardation of the same location at multiple angles. In tissue imaging with OCT, the retardation measured is only the "apparent birefringence" in which the birefringence value is only valid at the specific angle being measure because the optical axis of the organized tissue, e.g., tissue with birefringence property, is not always parallel to the surface of the tissue nor perpendicular the k-vector, e.g., propagation direction) of the incident light. This "apparent birefringence" is a reduced value compared to the "true birefringence" that is obtained when the k-vector is perpendicular to the optic axis of the tissue. This is because the magnitude of birefringence depends not only on the degree of optical anisotropy of the material, e.g., the organize tissue, but also on how the organize tissue is oriented relative to the k-vector of the propagating light wave. The phase retardation is related to birefringence of the material by the following relations: Phase retardation=L*Δn, where L is the length of the material in which light travels through and Δn is the "apparent birefringence." The apparent birefringence is $\Delta n = |n - n_o|$, wherein $n_o$ is refractive index of the ordinary and $$\frac{1}{n^2} = \frac{\sin^2\theta_c}{n_e^2} + \frac{\cos^2\theta_c}{n_o^2},$$

wherein $\vartheta_c$ is the angle between the k-vector and the optic axis.

Still referring back to FIG. 5A, when the k-vector is perpendicular to the optic axis, $\vartheta_c = 90$.degree., in which $n = n_e$ and $\Delta n = |n_e - n_o|$. However, when the k-vector is parallel to the optic axis, then $\vartheta_c = 0°$, in which $n = n_o$ and $\Delta n = 0$. In reality, k-vector is likely to be at some angle to the optic axis most of the time; therefore, the birefringence is in between 0 and $|n_e - n_o|$. In other words, when the birefringence values of the tissue are measured at an angle non-perpendicular to the optical axis, the birefringence is reduced compared to the maximum value and therefore the image contrast between organize and non-organized tissue is reduced. By measuring the birefringence of the sample at multiple angles, the maximum or the strong birefringence of the tissue can be determined to maximize the phase retardation contrast. An example is demonstrated from the reference by N. Ugryumova, S. V. Gangnus, S. J. Matcher, "Variable-angle-of-incidence polarization-sensitive optical coherence tomography: its use to study the 3-D collagen structure of equine articular cartilage," Pro. Soc. Photo. Opt. Instrum. Eng., 6079 (2006) 60792C-1.

Still referring back to FIG. 5A, one benefit that may be derived from having multiple data sets corresponding to the same region is if the scans are acquired sequentially then the SNR of that particular region may improve by data averaging at common points. Alternatively, having multiple data sets corresponding to the same region would enable selectively filtering the data sets for the one with the best SNR providing a clearer image of the region than its counterparts.

Still referring back to FIG. 5A, yet another benefit that may be derived from having multiple data sets corresponding to the same region when employing a constituent OCT system that acquires a PSOCT image as described above, would be the ability to acquire directional data that is not available from one acquisition direction in another acquisition direction. This would result in further enhancement of the image due to the acquisition of further accurate, or otherwise absent, retardance information at the region. When generating a PSOCT image from a multi-fiber probe, the directional orientation of the A-scans relative to the region is taken into consideration and the received signals are processed to account for such a directional orientation difference among the different fibers.

Figure 11:
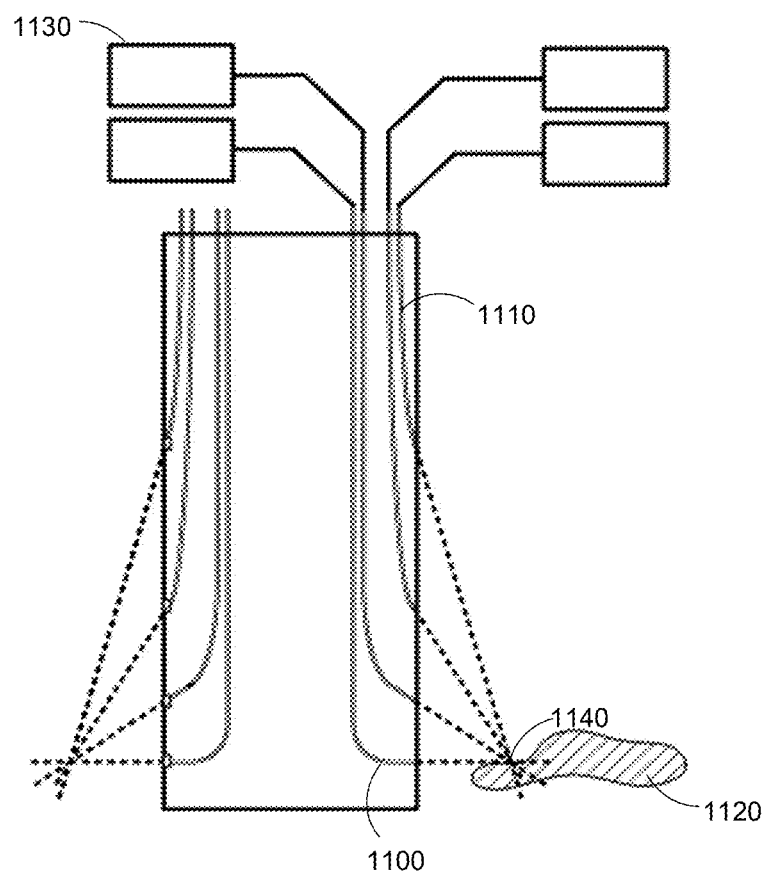
FIG. 11 is a diagram illustrating a cross section of an example PSOCT probe head acquiring an image scan from a sample.

Referring to FIG. 11, this diagram illustrates a cross-sectional view of an example OCT Probe having a rectangular prism shaped probe head containing four rows of linearly arranged fibers, in accordance with an embodiment of the present disclosure. The first row 1100 of fibers are spatially arranged such that the propagation axis of the beam emitted from the probe is directed at an angle of 90.degree. relative to the long axis of the probe. The following three fiber rows are arranged to have respective propagation axes at greater angles, to up to the last row of fibers 1110 that are oriented with respective propagation axes at an angle of 170.degree. relative to the longitudinal axis of the probe. Each one of the fibers is connected to its own constituent OCT subsystem shown as the boxes 1130.

Still referring to FIG. 11, the fibers that terminate on the right side of the probe may be employed to generate a PSOCT scan of the sample 1120. The A-scans acquired by the fibers can be seen to overlap at the region 1140. Given that the polarized illumination used to acquire the A-scan by the fiber 1100 is substantially parallel to the surface of the sample at region 1140 its A-scan would likely be lacking a reflectance signal containing the information required to visualize the tissues flat surface at the acquisition point 1140. However, since the three other fibers are also capable of scanning the same point 1140 at different angles, the reflectance signal they may acquire can be used to augment the A-scan acquired via the fiber 1100 to provide a more complete scan of the region. Furthermore the four scans acquired via the fibers may be combined and compared, or averaged to produce a more interpretable anisotropic map of the portion of the region 1140 in which the beams from the fibers spatially overlap.

Still referring to FIG. 11, in addition to acquiring multiple datasets of the same region simultaneously, other acquisition schemes may be employed to improve imaging of the overlapped region. For example, especially if two or more of the respective OCT subsystems share a common optical bandwidth, it may be advantageous to have the OCT subsystems acquire A-scans overlapping with the region 1140 one at a time. This would be advantageous in that when computing the OCT image data visualization the data that would be used for the region 1140 may be chosen from the multiple data sets acquired for that region from the multiple A-scans of the multiple constituent OCT systems.

Still referring to FIG. 11, in one example implementation, the best image data set for that region 1140 could be used by comparing the signal-to-noise ratio amongst the many available data sets at that region and choosing the data set with the highest value. Although the region 1140 is referred as a region, this is merely an example case; and this region may actually be a point in space and may be represented by a voxel (or pixel) or group of voxels (or pixels) in a 3D (or 2D or 1D) visualization of the OCT image data acquired by the OCT probe as herein disclosed.

Still referring to FIG. 11, in one example embodiment, the different OCT subsystems may have different associated wavelengths (or wavelength bands), permitting the acquisition of hyperspectral OCT data. For example, in the example embodiment shown in FIG. 11, the different OCT subsystems may be a set of hyperspectral OCT subsystems, such that the probe is capable of acquiring hyperspectral OCT data, where different hyperspectral channels correspond to different spatial directions incident on a common spatial region. This may be accomplished by designing each of the constituent OCT systems that overlap the region such that they employ varying illumination wavelengths (or range of wavelengths) to interrogate the region. By employing a large range of wavelengths to interrogate a single region, the hyperspectral response of that region may be acquired and used to analyze the imaged region.

Figure 12:
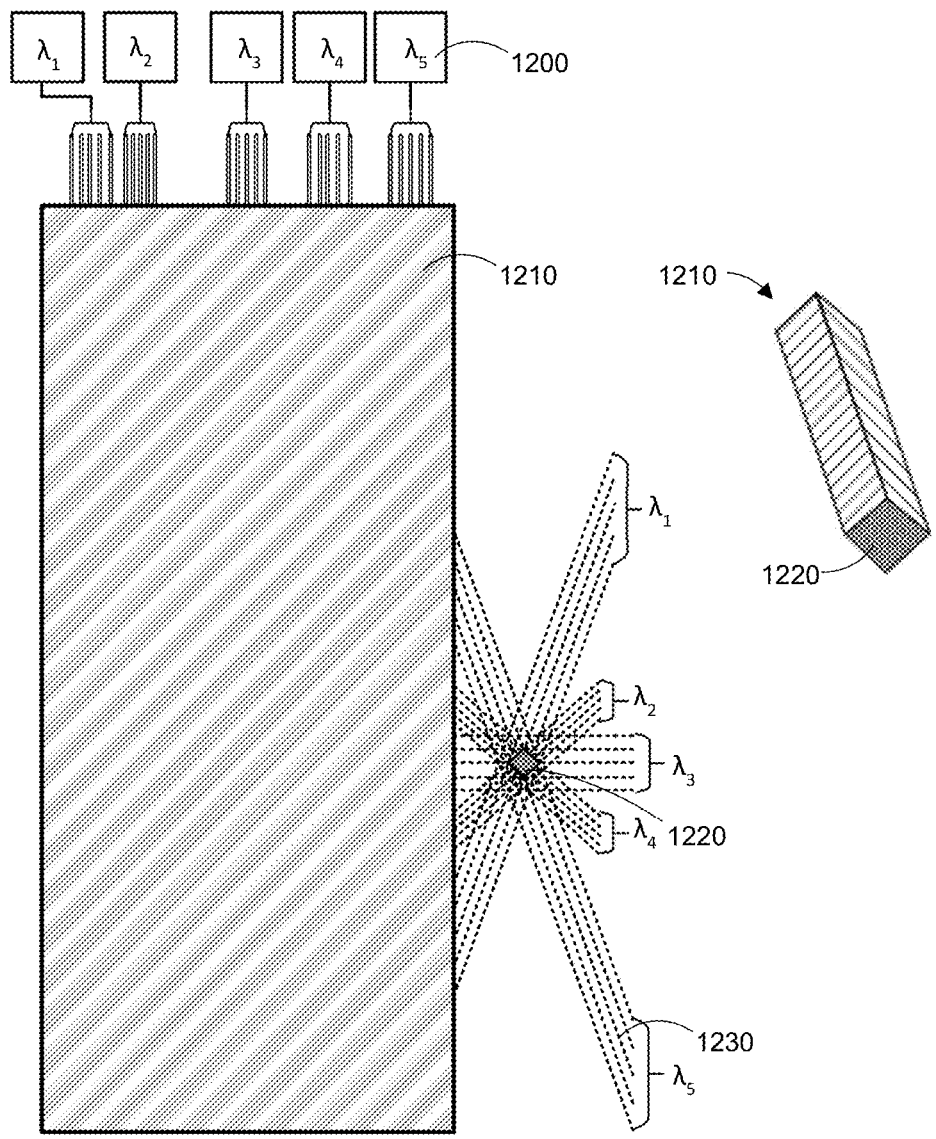
FIG. 12 is a diagram illustrating a cross section of an example hyperspectral OCT probe head acquiring an image scan of a volume.

Referring to FIG. 12, this diagram illustrates a cross-sectional view of an example embodiment of the OCT probe, in accordance with an embodiment of the present disclosure. The figure illustrates an OCT probe head employing 25 constituent OCT subsystems (not shown), embedded with their 25 sample arms 1210. The subsystems are split into groups of five wherein each group acquires OCT image data using differing interrogation illumination wavelength bands ($\lambda_1, \ldots, \lambda_5$) outlined by the boxes 1200. The 25 constituent OCT systems are used to acquire 25 A-scans along the 1D paths shown as 1230. These paths intersect in the region 1220 wherein all points contained within are overlapped by at least a single scan from a constituent OCT system employing each of the 5 interrogation wavelength bands ($\lambda_1, \ldots, \lambda_5$) outlined by the boxes 1200. Thus, the hyperspectral response of any of the points contained within the region 1220 may be attained at the five wavelength bands ($\lambda_1, \ldots, \lambda_5$) outlined by the boxes 1200 and subsequently used to provide further information about the region.

Still referring to FIG. 12, although any wavelength range may be chosen to interrogate the sample, given that the illumination is to penetrate the surface of the sample to participate in OCT interferometry this may prevent the acquisition of hyperspectral data using wavelengths that cannot penetrate the surface of the sample, thereby potentially limiting the spectral range over which the hyperspectral signature may be acquired in the sample volume. However, spectral signatures need not be exhaustive; and, thus, even a limited spectral signature may be of use in benefiting the user, for example, when identifying tissue, or the presence of various pathologies. The probe head is shown in the figure as a cross-section of a rectangular prism-type probe head having rows of fibers in the same orientation as the cross-section only stacked along the normal direction to the plane of the cross section shown. Having this rectangular prism-type probe head would allow for the acquisition of hyperspectral data on a volumetric subsurface region in a sample of the form of the elongated volume 1210.

Figure 13:
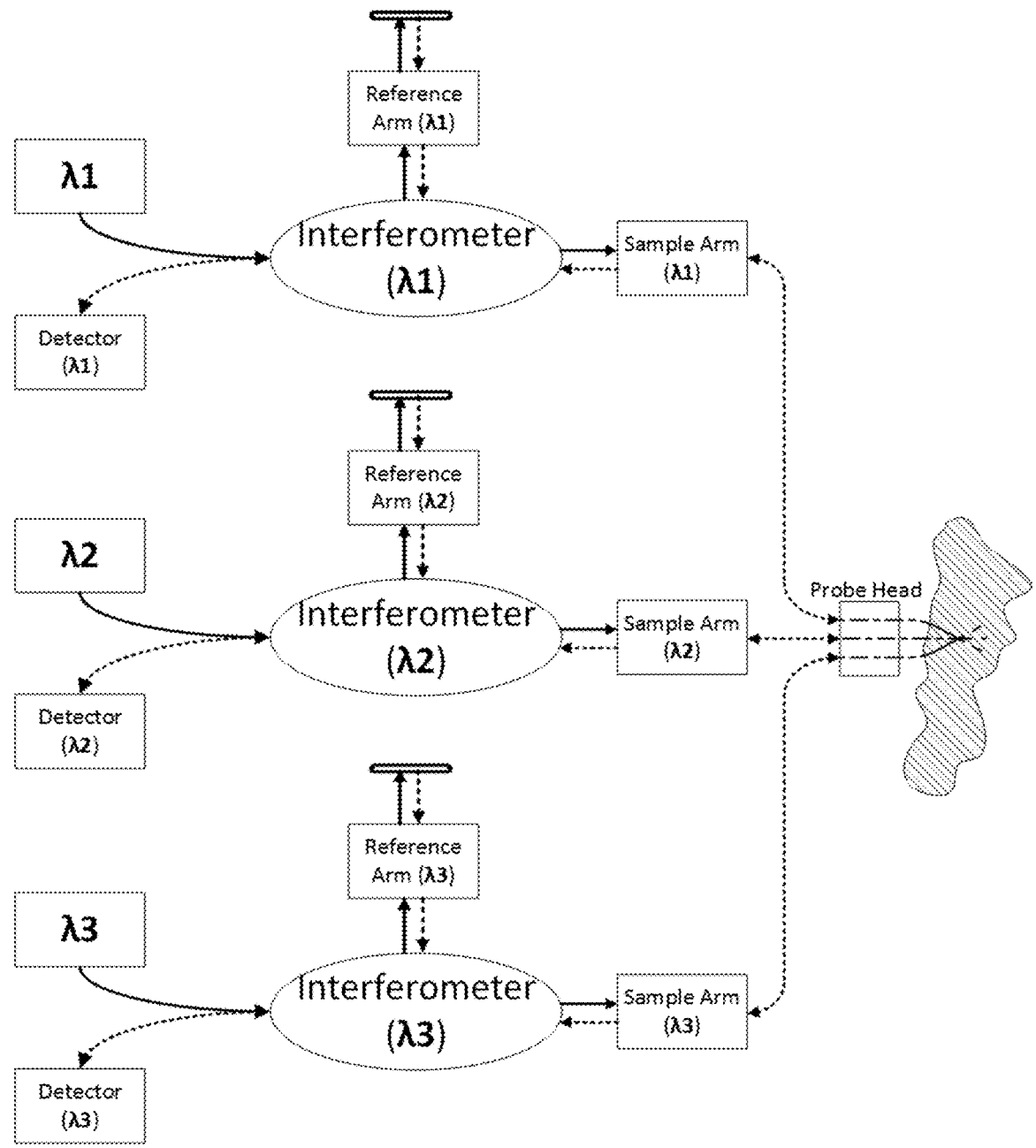
FIG. 13 is a diagram illustrating an exemplary illumination spectrum of an example hyperspectral OCT probe system.

Referring to FIG. 13, this diagram illustrates an example OCT system employing multiple wavelengths for multi-spectral imaging, in accordance with an embodiment of the present disclosure. In the example system, three different laser wavelengths were used to interrogate the sample. The example wavelengths are $\lambda_1=1064$ nm, $\lambda_2=1310$ nm and $\lambda_3=1550$ nm, each with a bandwidth of 100 nm. The three sources are each coupled to their respective interferometer with operating wavelength between 1024 nm-1104 nm for the 1064-nm laser, 1270 nm-1350 nm for the 1310-nm laser and 1510 nm-1590 nm for the 1550-nm laser. Each interferometer is in optical communication with a respective optical fiber within the probe head, which focuses the light and side fires it onto the sample at the side of the multi-fiber OCT probe. The probe may be pulled back for 2D imaging and a composite image can be obtained by correlating the different images (from different excitation wavelength) through shifting the images by the known distances between the optical fibers. The incident light from a given optical fiber is reflected or scattered by the sample back to a respective OCT subsystem, where the reflected or scattered light enters the interferometer and interferes with its respective signal from the reference arm. The interfered OCT signal is then detected by the respective detectors, which in this example case are InGaAs detections sensitive in the wavelength range between 800 nm-1700 nm.

Still referring to FIG. 13, in some embodiments, a processor 115 may amalgamate the A-scans into a single OCT image visualization to be displayed on a display 125. This may be accomplished by superimposing the scans into a common image space wherein the individual's A-scan projections in the image space are dependent on the spatial position and orientation of the individual optical fibers from which they were acquired. In some embodiments, the A-scans may spatially overlap over one or more regions in the image space, and in such a case, further processing may be employed to provide a composite image of the overlapping region.

Figure 14A:
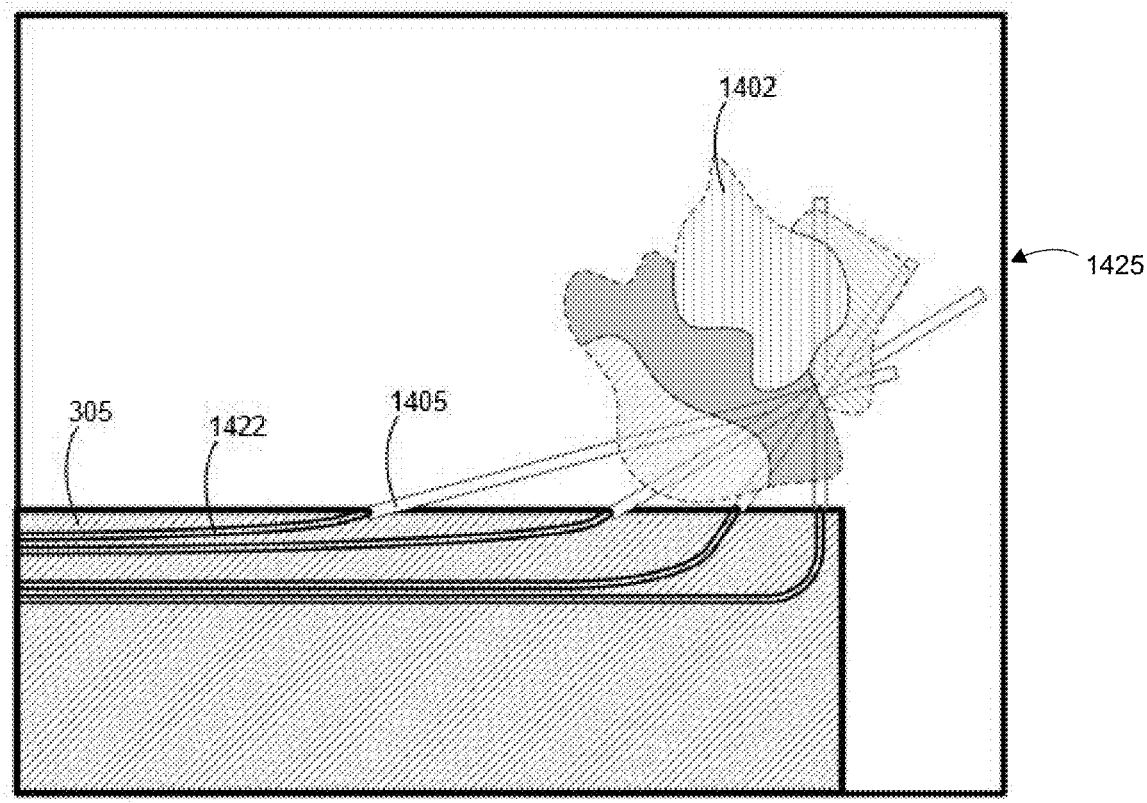
FIGS. 14A and 14B are diagrams, together, illustrating the formation of an OCT visualization from an example OCT probe in an image space.
Figure 14B:
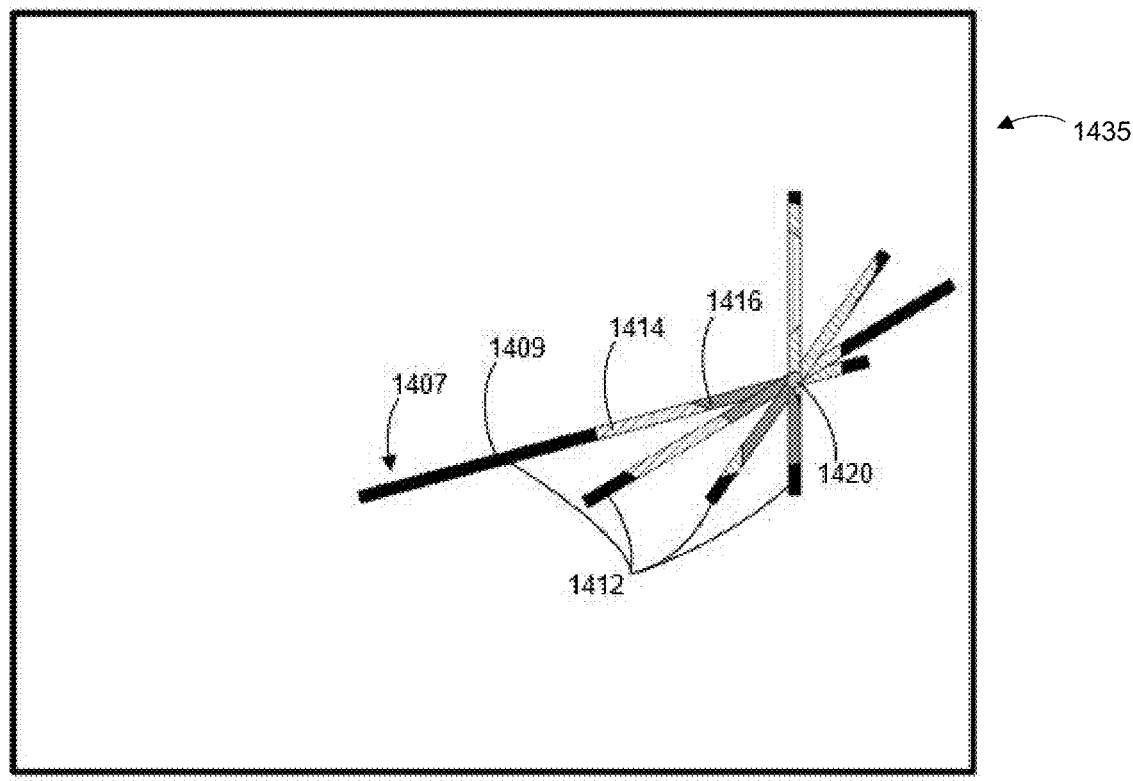

Referring to FIGS. 14A and 14B, together, these diagrams illustrate an example of OCT image acquisition by multiple fibers and its subsequent generation as a visualization in an image space, in accordance with embodiment of the present disclosure. FIG. 14A shows a multi-fiber OCT probe 305 having fibers 1422 acquiring A-scans along the incident paths 1405 of the non-uniform tissue sample 1402 in the physical coordinate space 1425. FIG. 14B depicts the visualization of the acquired A-scans in an image space. Generally, in order to generate visualizations of the acquired A-scan image data in the image space, the spatial positions of the incident paths along which the A-scans were acquired must be known relative to one another. Using this meta-data, e.g., the spatial relation of the incident paths of the acquired A-scans, each A-scan may be visualized in an image space while retaining the spatial coherence of the sample that was scanned, by minimizing any artefacts and image distortion introduced during the generation of the OCT image.

Still referring to FIGS. 14A and 14B, together, for example, as shown in FIG. 14B, each of the visualized A-scan projections 1412 in the image space 1435 depicts the interaction of the interrogating illumination with the sample 1402 along the incident paths 1405. The example A-scan 1407 has multiple segments reflective of the response of the interrogating illumination to the different regions of the segmented sample 1402. To elaborate further, the uppermost section 1409 of the A-scan 1407 is dark showing no significant interaction with any matter while the following segment 1414 differs from the previous section in that the light interacts differently over this region with respect to region 1409. While the following segment 1416 differs from both of the previous segments emphasized by its alternate pattern. The differences among the sections result from the varying optical properties of different regions within the sample 1402. The segmentation of the A-scans depicted in the example image space 1435, although reflective of differences in tissue, in practice, do not necessarily have such well-defined boundaries and may actually be visualized using different contrasts, colors, and dynamic ranges. The diagrams shown in FIGS. 14A and 14B are example depictions only and should not be taken to limit the embodiments of the OCT probe system as disclosed herein.

Still referring to FIGS. 14A and 14B, together, in the case of overlapping A-scans such as at the region 1420 shown in FIG. 14B it may be advantageous to apply further processing to the region instead of projecting all of the A-scan visualizations to overlap at the given region, as this may degrade the ability of a user to infer beneficial information due to the potential saturation of the image located in that region. Several different methods may be used to process the overlapping data that may provide further benefit to the user. For example, one method with a fast processing time involves using data from the first acquired A-scan that overlaps the point and ignoring the subsequently acquired A-scans that also subsequently overlap with the point. Alternatively, a signal-to-noise ratio may be computed for each A-scan and the A-scan with the highest ratio may be the one visualized at the overlapping region. Alternatively, image data from the one or more overlapping A-scan segments may be averaged, and the resulting signal value visualized and displayed in the overlapping region. Many alternative ways of processing such a region with overlapping A-scans may be employed, and further, the examples provided herein to process image data for such an overlapping region are provided as examples only and should not be taken to limit the scope of methods of visualizing said region having overlapping A-scans. Furthermore the processing of image data for an overlapping region and further for any applicable visualized region may take into account, amongst other factors hyperspectral image data, PSOCT image data, and any A-scan image data acquired as per the OCT probe disclosed herein or other OCT probes used in conjunction. External data may also be taken into account in processing such as by manually or automatically segmenting the image space for anatomical significance and biasing the data based on wavelength range used among other methods.

Figure 15:
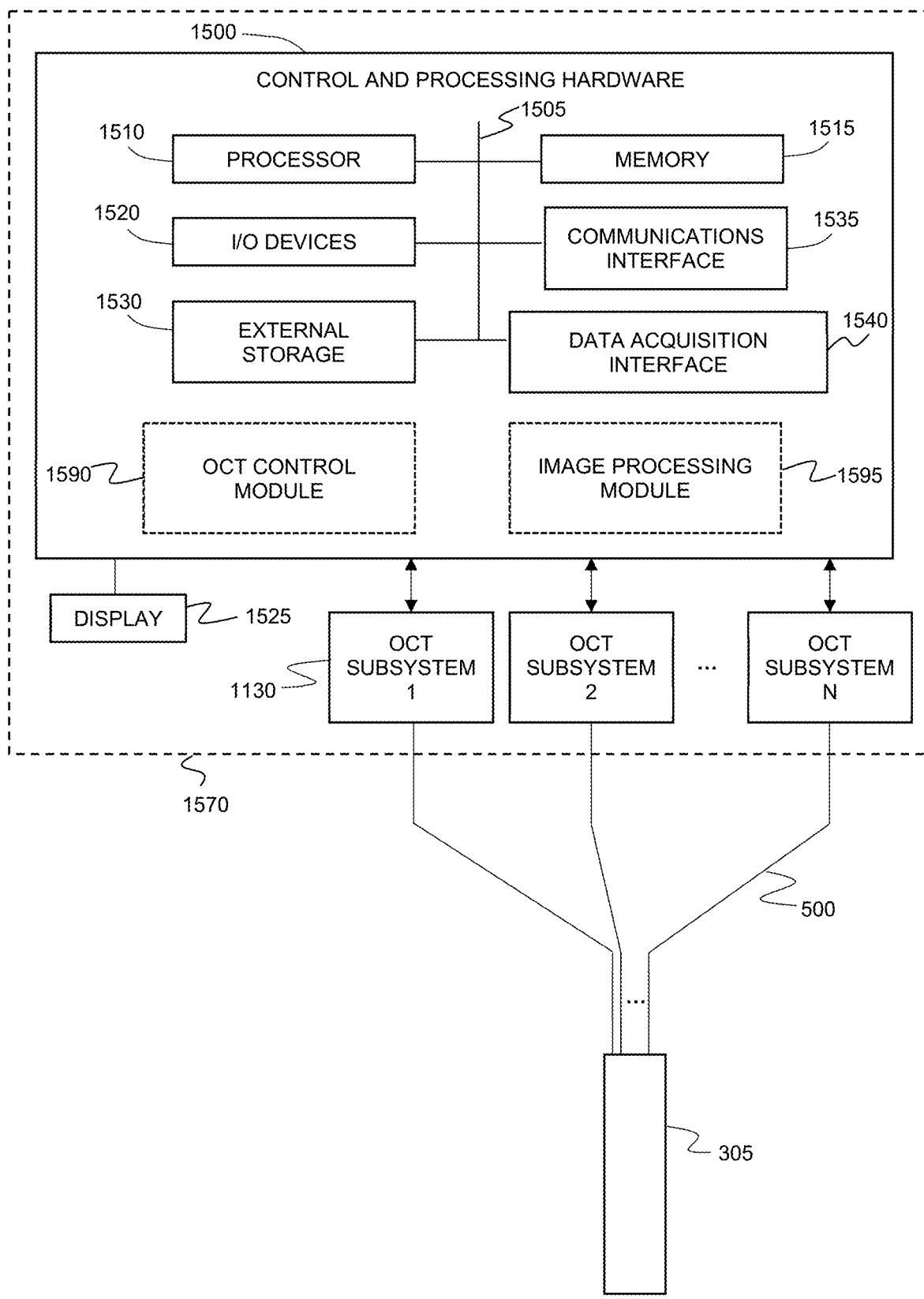
FIG. 15 is a diagram illustrating an example of a system for performing OCT measurements using a multi-fiber probe.

Referring to FIG. 15, this diagram illustrates an example radiotherapy system for performing OCT measurements with a multi-fiber optical probe, in accordance with an embodiment of the present disclosure. The example system comprises a multi-fiber probe 305, which houses a plurality of optical fibers, as described above. In the example embodiment shown, each fiber 500 is in optical communication with a respective OCT subsystem 1130. Each OCT subsystem is operatively coupled to the control and processing hardware 1500. The OCT subsystems 1130 may optionally be directly integrated into a control and processing device 1570, or may be provided as external devices.

Still referring to FIG. 15, the control and processing hardware 1500 comprises a processor 1510, a memory 1515, a system bus 1505, one or more input/output devices 1520, a plurality of optional additional devices, such as communications interface 1535, a display 1525, an external storage 1530, and a data acquisition interface 1540. In one example implementation, the display 1525 may be employed to provide a user interface for receiving user input to control the operation of the system and/or to display images received and processed by the system. The display may be directly integrated into a control and processing device 1570 (for example, as an embedded display), or may be provided as an external device (for example, an external monitor).

Still referring to FIG. 15, the aforementioned example methods for processing OCT image data received by the OCT subsystems 1130 can be implemented via processor 1510 and/or memory 1515. The executable instructions, represented as OCT control module 490, may be processed by control and processing hardware 400 to control the operation of the OCT subsystems, for example, for the sequential or parallel acquisition of OCT image data. The control and processing hardware 1500 may also include executable instructions for generating a composite volumetric image based on OCT image data, as per the example methods described above or variations thereof, as represented by image processing module 1595.

Still referring to FIG. 15, the methods described herein can be partially implemented via hardware logic in processor 1510 and partially using the instructions stored in memory 1515. Some embodiments may be implemented using processor 1510 without additional instructions stored in memory 1515. Some embodiments are implemented using the instructions stored in memory 1515 for execution by one or more microprocessors. Thus, the present disclosure is not limited to a specific configuration of hardware and/or software.

Still referring to FIG. 15, the example system shown in the figure is not intended to be limited to the components that may be employed in a given implementation. For example, the system may include one or more additional processors. Furthermore, one or more components of control and processing hardware 1500 may be provided as an external component that is interfaced to a processing device. Furthermore, although the bus 1505 is depicted as a single connection between all of the components, the bus 1505 may represent one or more circuits, devices, or communication channels which link two or more of the components. For example, the bus 305 may include a motherboard. The control and processing hardware 1500 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSIs), application-specific integrated circuits (ASICs), or firmware such as electrically erasable programmable read-only memory (EEPROMs) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

The specific embodiments described above have been shown by way of example, and these embodiments may be susceptible to various modifications and alternative forms. The claims are not intended to be limited to the particular forms disclosed, but, rather, cover all modifications, equivalents, and alternatives falling within the spirit and scope of the present disclosure.

What is claimed is:

1. A method of providing a hyperspectral multichannel optical coherence system, the method comprising providing image processing computer hardware configured to:
    process optical coherence tomography (OCT) signals obtained from a plurality of OCT subsystems, thereby obtaining an OCT image dataset comprising a plurality of OCT A-scans and hyperspectral image data; and
    process the OCT image dataset to generate volumetric image data based on known positions and known orientations of a plurality of external beam paths associated with the plurality of OCT subsystems, the volumetric image data represented in a common reference frame for rendering a composite volumetric image,
    whereby at least one parameter of each of OCT subsystem of the plurality of OCT subsystems is independently adjustable.

2. The method of claim 1, wherein the image processing computer hardware is further configured to render the composite volumetric image on a display.

3. The method of claim 1, further comprising the plurality of OCT subsystems, each OCT subsystem of the plurality of OCT subsystems respectively comprising a plurality of elements, the plurality of elements comprising one of:
    a combination of a same optical source and a same optical detector; and
    a combination of a distinct optical source and a distinct optical detector,
    each OCT subsystem individually configured to attain an individualized OCT scan, independent of another OCT subsystem, and
    each OCT subsystem individually configured to adjust at least one parameter of each element of the plurality of elements thereof, independent of another OCT subsystem.

4. The method of claim 1, further comprising a plurality of single mode optical fibers supportable by a housing, a proximal end of each single mode optical fiber of the plurality of single mode optical fibers respectively in optical communication with each OCT subsystem such that each single mode optical fiber of the plurality of single mode optical fiber respectively operates as at least a distal portion of a sample beam path for each OCT subsystem.

5. The method of claim 4, further comprising a plurality of distal optical elements, each distal optical element of the plurality of distal optical elements respectively in optical communication with a distal end of each single mode optical fiber of the plurality of single mode optical fibers for at least one of focusing optical radiation emitted therefrom along a respective external beam path of a plurality of external beam paths, collimating the optical radiation emitted therefrom along the respective external beam path of the plurality of external beam paths, and collecting scattered optical radiation that is scattered along the respective external beam path of the plurality of external beam paths, and the plurality of external beam paths being external to the housing.

6. The method of claim 1, wherein the OCT image dataset comprises OCT image data from the plurality of A-scans that are spatially overlapped within an overlapping region.

7. The method of claim 1,
    wherein a plurality of points, contained within a region external to the housing, are overlapped by at least one scan from each OCT subsystem employing a distinct interrogation wavelength band of a plurality of distinct interrogation wavelength bands,
    wherein a hyperspectral response, corresponding to any of the points, contained within the region external to the housing, is attained at the distinct interrogation wavelength band,
    wherein the hyperspectral response is used to provide further information relating to the region external to the housing, and
    wherein the plurality of distal optical elements further comprises a reference mirror and a reference arm.

8. The method of claim 1, wherein the at least one parameter comprises at least one of:
    a distinct wavelength range of each optical source of each OCT subsystem, whereby the plurality of OCT subsystems is optimizable for a particular tissue type,
    a distance between each reference mirror and each corresponding reference arm, whereby the plurality of OCT subsystems is optimizable for one of a particular depth and a particular illumination wavelength, and
    wherein the image processing computer hardware is further configured to one of:
    spatially average the OCT image dataset within the overlapping region;
    select OCT image data within the overlapping region that has a highest signal-to-noise ratio for inclusion in the volumetric image data; and
    spatially interpolate the OCT image dataset when generating the volumetric image data.

* * * * *